(12) United States Patent
Thakur et al.

(10) Patent No.: US 10,093,665 B2
(45) Date of Patent: Oct. 9, 2018

(54) SOLID ORAL FORMULATIONS AND CRYSTALLINE FORMS OF AN INHIBITOR OF APOPTOSIS PROTEIN

(71) Applicant: Novartis AG, Basel (CH)

(72) Inventors: Jeewan Thakur, Basel (CH); Dong Yang, Parsippany, NJ (US); Lili Feng, Pine Brook, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/364,841

(22) Filed: Nov. 30, 2016

(65) Prior Publication Data

US 2017/0081319 A1 Mar. 23, 2017

Related U.S. Application Data

(63) Continuation of application No. 14/095,313, filed on Dec. 3, 2013, now Pat. No. 9,540,363, which is a continuation of application No. 13/388,149, filed as application No. PCT/EP2010/061679 on Aug. 11, 2010, now Pat. No. 8,623,385.

(60) Provisional application No. 61/274,051, filed on Aug. 12, 2009.

(51) Int. Cl.
| | |
|---|---|
| C07D 417/04 | (2006.01) |
| A61K 9/00 | (2006.01) |
| A61K 38/00 | (2006.01) |
| A61K 31/427 | (2006.01) |
| A61K 9/20 | (2006.01) |

(52) U.S. Cl.
CPC .......... *C07D 417/04* (2013.01); *A61K 9/2018* (2013.01); *A61K 9/2027* (2013.01); *A61K 9/2054* (2013.01); *A61K 9/2077* (2013.01); *A61K 31/427* (2013.01); *C07B 2200/13* (2013.01)

(58) Field of Classification Search
CPC .. A61K 9/2018; A61K 9/2027; A61K 9/2054; A61K 31/427; A61K 9/2077; C07D 417/04; C07B 2200/13
See application file for complete search history.

(56) References Cited

FOREIGN PATENT DOCUMENTS

| | | |
|---|---|---|
| WO | 2003014732 A1 | 2/2003 |
| WO | 2004/005248 | 1/2004 |
| WO | 2005/097791 | 10/2005 |
| WO | 2006069063 A1 | 6/2006 |
| WO | 2008/016893 | 2/2008 |

OTHER PUBLICATIONS

Polymorphism in pharmaceutical solids edited by H. G. Brittain, Marcel Dekker, 1999; D.J.W. Grant (chapter 1) ; p. 1-10 and J. K Guillory (chapter 5); p. 183-226.

Byrn et al.,"Pharmaceutical Solids: A Strategic Approach to Regulatory Considerations", Pharmaceutical Research, 1995, 12(7): 945-954.

Bastin et al., "Salt Selection and Optimisation Procedures for Pharmaceutical New Chemical Entities", Organic Process Research & Development, 2000, vol. 4, No. 5, pp. 427-435.

Takada, "API form screening and selection in drug discovery stage", Pharm Stage, 2007, vol. 6, No. 10, pp. 20-25, English translation.

Ohshima, "Crystallization of Polymorphs and Pseudo-polymorphs and its Control", Pharm Stage, 2007, vol. 6, No. 10, pp. 48-53, English translation.

Kojima et al., "Effective selection of crystal form in pharmaceutical development: Application of Raman Spectroscopy to salt and polymorph screenings", Pharm Tech Japan, 2007, vol. 23, No. 12, pp. 173(2461-181(2469), English translation.

Kojima et al., "Improvement of physical stability of crystalline drug candidate compound by selection of salt and crystal form", Journal of Pharmaceutical Science and Technology, Japan, 2007, vol. 67, Supp., pp. 426, English translation.

Stahly, "Importance of drug salt selection and screening of crystal polymorph", Journal of Pharmaceutical Science and Technology, Japan, 2006, vol. 66, No. 6, pp. 435-426, English translation.

Matsumoto et al., Yakuzai-gaku Manual (Pharmaceutical Manual), Japan, 1989, First edition, pp. 28, English translation.

PFSB, "Setting of standards and tests for new drugs", PMSB/ELD Notification No. 568, issued by Evaluation and Licensing Division, Pharmaceutical Safety Bureau, Ministry of Health, Labor and Welfare, May 1, 2001, English translation.

Polyvinylpyrrolidone K 30, from http://www.sigmaaldrich.com/catalog/product/fluka/81420?lang=en&region=US, pp. 1-3, accessed May 12, 2015.

Wet granulation, from http://www.dfepharma.com/en/knowledge-base/oral-solid-dose/wet-granulation.aspx, pp. 1-7, accessed May 14, 2015.

Singhal et al., 2004, "Drug polymorphism and dosage form design: a practical perspective", ADDR, 56(3):335-347.

Augsburger, Tablets and capsules: Design and formulation, pp. 1-102, published in spring, 2003, available online Oct. 2002.

Patil, The effect of different excipient on Aceclofenac, Deccan J. Pharmaceutics & Cosmetology, 2011, 2, pp. 27-40.

The European Agency for the Evaluation of Medicinal Products—Evaluation of Medicines for Human Use, pp. 1-10, published on Feb. 20, 2003.

Muller et al, Nanosuspensions as particulate drug formulations in therapy Rationale for development and what we can expect for the future, Advanced Drug Delivery Reviews, 2001, 47, pp. 3-19.

(Continued)

*Primary Examiner* — Julie Ha
*Assistant Examiner* — Li N Komatsu
(74) *Attorney, Agent, or Firm* — Scott W. Reid

(57) ABSTRACT

The present disclosure relates to crystalline form of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, salts and hydrates thereof. This disclosure also relates to solid oral formulation of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, pharmaceutically acceptable salts, solvates (including hydrates) thereof, as well as methods of treatment using the same.

27 Claims, 20 Drawing Sheets

(56) References Cited

OTHER PUBLICATIONS

Caira M R "Crystalline Polymorphism of Organic Compounds", Topics in Current Chemistry, vol. 198, pp. 163-208, Jan. 1998.
Sune-Negre, Jose, "New Galenic Contributions to the Administration Forms" 2002.
Pharmaceutical Drug: Wikepedia htt;://en.wikipedia.org/wiki/Pharmaceutical_drug downloaded Mar. 26, 2013.
Yin, S. et al., "Simulated PXRD Patterns in Studies of the Phase Composition and Thermal Behavior of Bulk Crystalline Solids", American Pharmaceutical Review, vol. 6, No. 2, p. 80, 2003.

SOLID ORAL FORMULATIONS AND CRYSTALLINE FORMS OF AN INHIBITOR OF APOPTOSIS PROTEIN

CROSS-REFERENCE TO RELATED APPLICATIONS

This application is a continuation of U.S. application Ser. No. 14/095,313, filed Dec. 3, 2013, now U.S. Pat. No. 9,540,363; which is a continuation of U.S. application Ser. No. 13/388,149, now U.S. Pat. No. 8,623,385; which is the National Stage of International Application No. PCT/EP2010/061679, filed Aug. 11, 2010, which is incorporated herein by reference, and which claims the benefit of the filing date of U.S. Application No. 61/274,051, filed 12 Aug. 2009.

FIELD OF THE INVENTION

The present disclosure relates to crystalline form of (S)—N—((S)-1-cyclohexyl-2-{(S)-2-[4-(4-fluoro-benzoyl)-thiazol-2-yl]-pyrrolidin-1-yl}-2-oxo-ethyl)-2-methyl-amino-propionamide, salts and hydrates thereof. This disclosure also relates to solid oral formulation of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, pharmaceutically acceptable salts, solvates (including hydrates) thereof, as well as methods of treatment using the same.

BACKGROUND ART

The compound (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, is described by Formula (I):

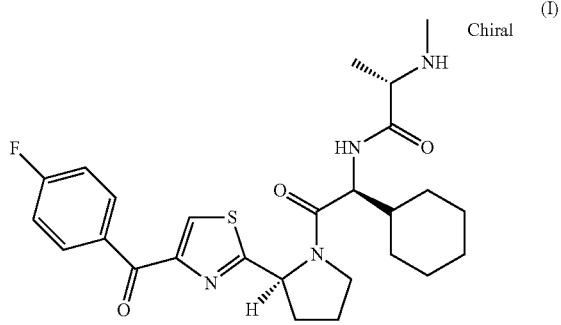 [SMILES: CN[C@@H](C)C(=O)N[C@H](C(=O)N1CCC[C@H]1c1nc(C(=O)c2ccc(F)cc2)cs1)C1CCCCC1]

and is an inhibitor of Apoptosis Protein (IAPs) that protect cancer cells from apoptotic cell death.

The compound of Formula (I) ("Compound (I)") is generally and/or specifically disclosed in WO05/097791 and WO08/016893, both of which are incorporated herein by references in their entirety.

SUMMARY OF THE INVENTION

The present disclosure is directed to oral formulations of (S)—N—((S)-1-cyclohexyl-2-{(S)-2-[4-(4-fluoro-benzoyl)-thiazol-2-yl]-pyrrolidin-1-yl}-2-oxo-ethyl)-2-methyl-amino-propionamide, including its salt(s) and/or solvate(s). Preferred embodiments of the present disclosure are directed to tablet formulations of (S)—N—((S)-1-cyclohexyl-2-{(S)- 2-[4-(4-fluor-benzoyl)-thiazol-2-yl]-pyrrolidin-1-yl}-2-oxo-ethyl)-2-methylamino-propionamide with high drug load with an immediate release profile. The compound (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, is described by Formula (I):

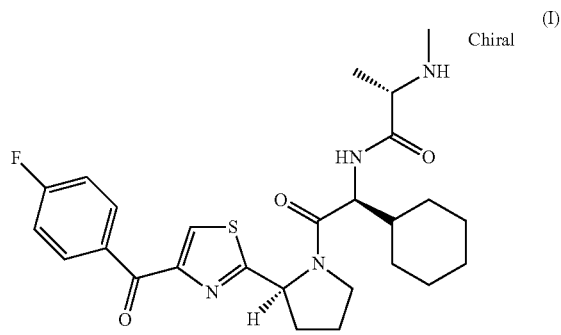 [SMILES: CN[C@@H](C)C(=O)N[C@H](C(=O)N1CCC[C@H]1c1nc(C(=O)c2ccc(F)cc2)cs1)C1CCCCC1]

The present disclosure also provides crystalline forms of (S)—N—((S)-1-cyclohexyl-2-{(S)-2-[4-(4-fluoro-benzoyl)-thiazol-2-yl]-pyrrolidin-1-yl})-2-oxo-ethyl)-2-methylamino-propionamide, including its salt(s) and/or solvate(s). In a first embodiment, the present disclosure relates to crystalline form $H_A$, which is a hemihydrate free form of the compound of Formula (I). In a second, third, fourth, and/or fifth embodiment, the present disclosure relates to crystalline form A, B, C and/or D, respectively, which is each an anhydrous free form of the compound of Formula (I).

BRIEF DESCRIPTION OF THE DRAWINGS

The invention is illustrated by reference to the accompanying drawing described below.

Figure 1:
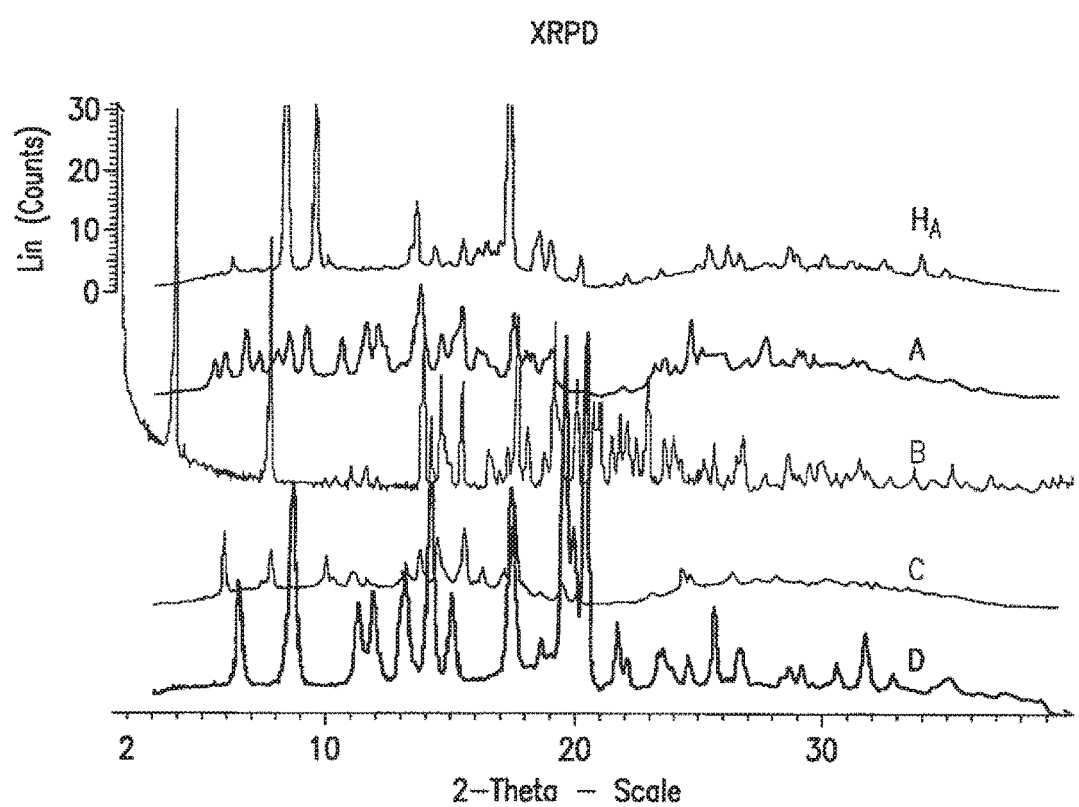
FIG. 1. illustrates the powdered X-ray diffraction (XRPD) patterns of Forms $H_A$, A, B, C and D of the compound of Formula (I).

DETAILED DESCRIPTION OF THE INVENTION (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide (structure depicted in Formula (I)) and its hydrate(s) exist in different forms. The disclosure provides, at least in part, the H$_A$, A, B, C, and D crystalline forms for the compound of Formula (I).

The crystalline forms of compound of Formula (I), its salts and solvates can be characterized by a number of methods, including but not limited to, Powder X-Ray diffraction (PXRD), simulated powder X-ray patterns (Yin. S.; Scaringe, R. P.; DiMarco, J.; Galella, M. and Gougoutas, J. Z., American Pharmaceutical Review, 2003, 6, 2, 80), Differential scanning calorimetry (DSC) experiments, Solid-state C-13 NMR measurements, (W. L. Earl and D. L. VanderHart, J. Magn. Reson., 1982, 48, 35-54), Raman spectroscopy, Infra-red spectroscopy, Moisture sorption isotherms (VTI—variable temperature isotherms), and hot stage techniques.

The forms may be characterized and distinguished using single crystal x-ray diffraction, which is based on unit cell measurements of a single crystal of a particular form at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder x-ray diffraction analysis in which the diffraction profile is compared to a simulated profile representing pure powder material, both run at the same analytical temperature, and measurements for the subject form characterized as a series of 2θ values.

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

Likewise, it is to be understood that any crystal forms that provide differential scanning calorimetry (DSC), thermogravimetric analysis (TGA), and/or moisture sorption isotherms patterns substantially identical to those disclosed in the accompanying Figures fall within the scope of the present invention. The ability to ascertain substantial identities of these patterns is within the purview of one of ordinary skill in the art.

Form H$_A$

Form H$_A$ can be synthesized according to Scheme A. Starting material B1 and B3 are commercially available.

Form H$_A$ is a crystalline hemihydrate with water content of ~1.7%. This form is slightly hygroscopic. Its water content stays ~1.7% between 10% relative humidity (RH) and 70% RH and takes additional ~0.4% of moisture from 70% RH to 95% RH. Upon heating to above 100° C., Form H$_A$ loses water and converts to Form B.

Form H$_A$ can be characterized by a powder x-ray diffraction pattern comprising three or more 2θ values selected from the group consisting of 8.3±0.2, 9.5±0.2, 13.5±0.2, 17.3±0.2, 18.5±0.2, and 18.9±0.2, at ambient temperature (i.e., at temperature from about 20° C. to 25° C.).

Form H$_A$ can be characterized by a powder x-ray diffraction pattern comprising four or more 2θ values selected from the group consisting of 8.3±0.2, 9.5±0.2, 13.5±0.2, 17.3±0.2, 18.5±0.2, and 18.9±0.2, at ambient temperature (i.e., at temperature from about 20° C. to 25° C.).

Form H$_A$ can be characterized by a powder x-ray diffraction pattern comprising five or more 2θ values selected from the group consisting of 8.3±0.2, 9.5±0.2, 13.5±0.2, 17.3±0.2, 18.5±0.2, and 18.9±0.2, at ambient temperature (i.e., at temperature from about 20° C. to 25° C.).

Form H$_A$ can be characterized by a powder x-ray diffraction pattern at ambient temperature (i.e., at temperature from about 20° C. to 25° C.), substantially in accordance with that shown in FIG. 1.

Figure 2:
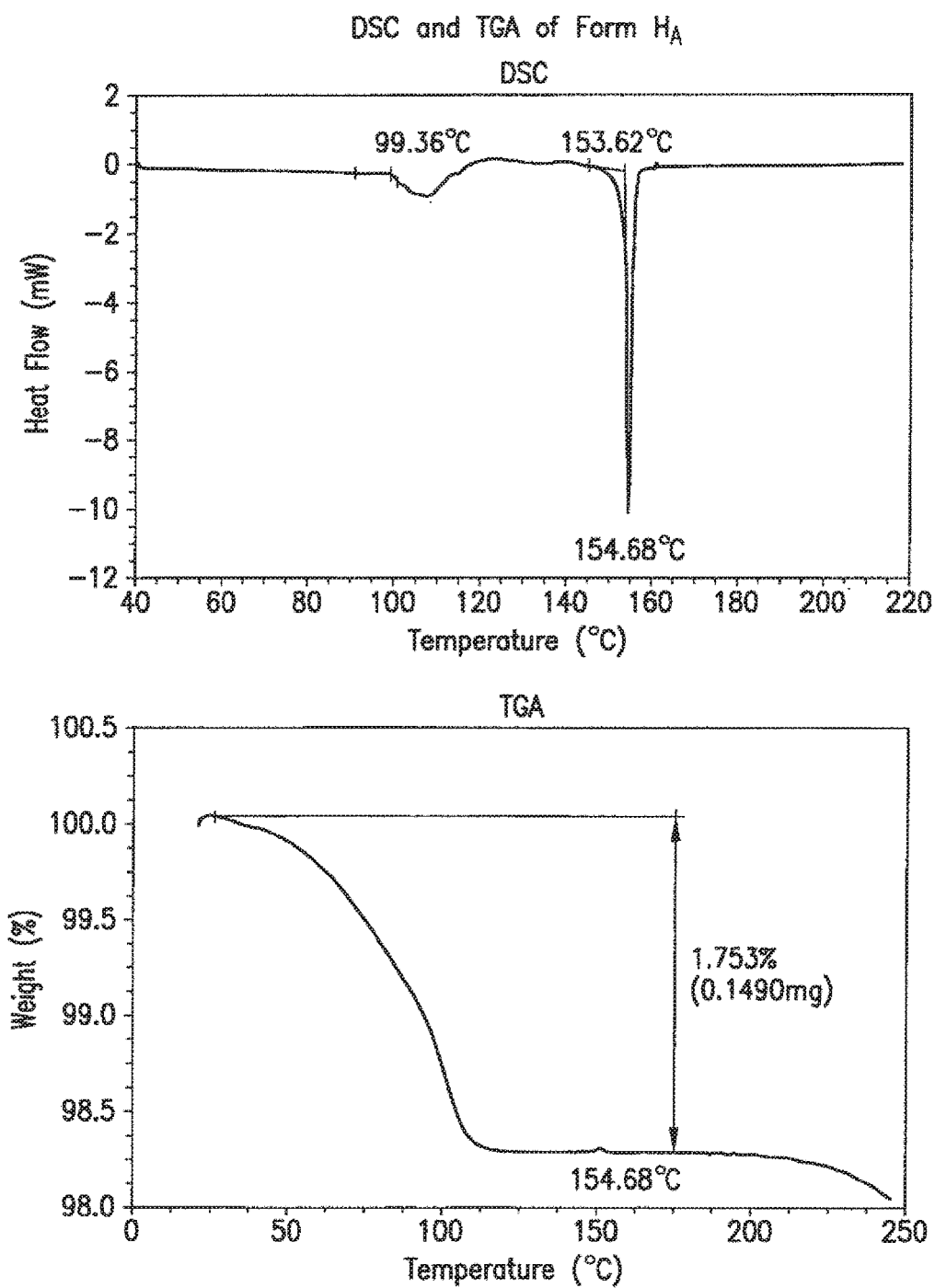
FIG. 2. illustrates the differential scanning calorimetry (DCS) pattern and thermogravimetric analysis pattern (TGA) of Form $H_A$ of the compound of Formula (I).

Form H$_A$ can be characterized by a differential scanning calorimetry (DSC) thermogram substantially in accordance with that shown in FIG. 2.

Form H$_A$ can be characterized by a thermo gravimetric analysis (TGA) diagram substantially in accordance with that shown in FIG. 2.

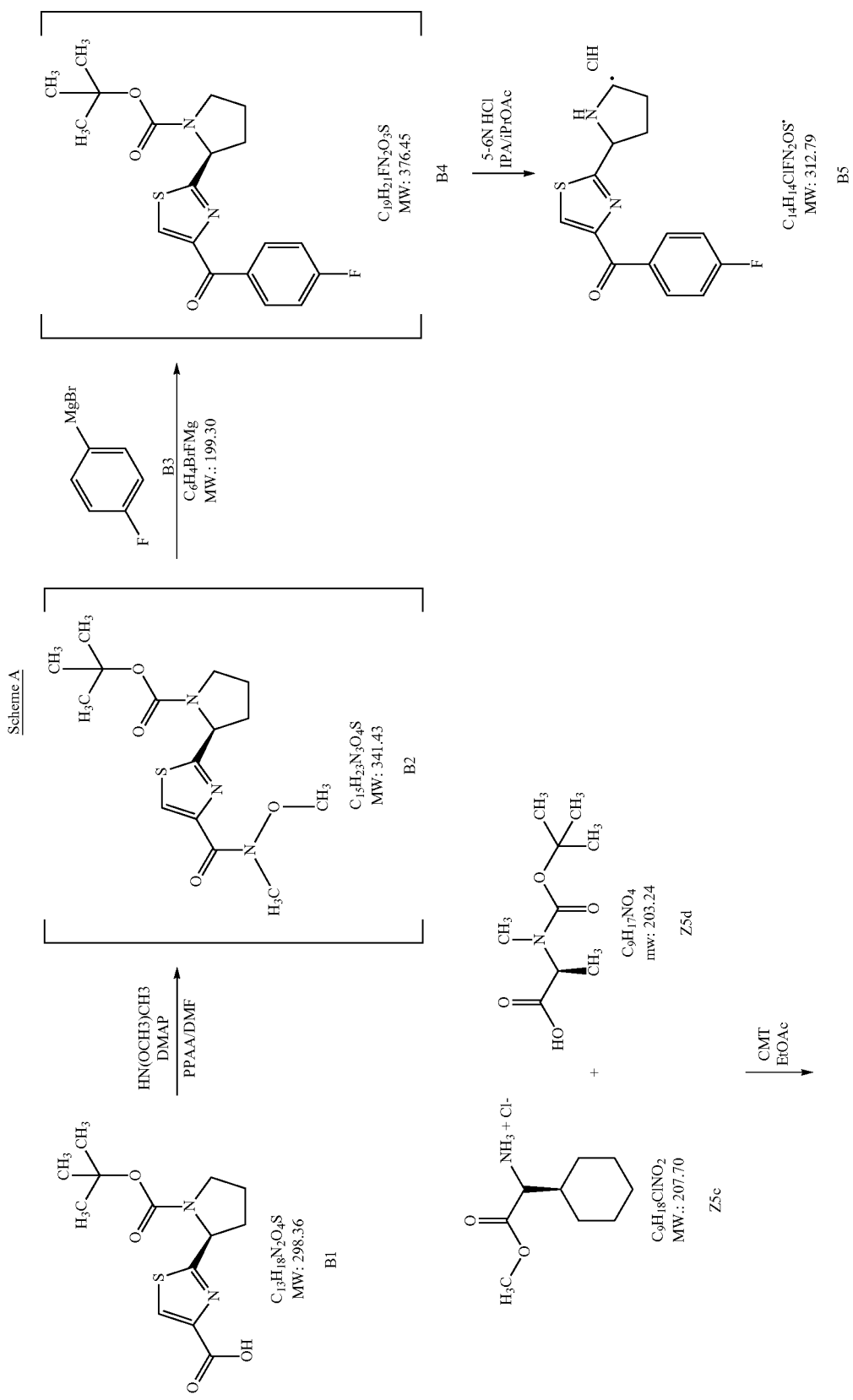

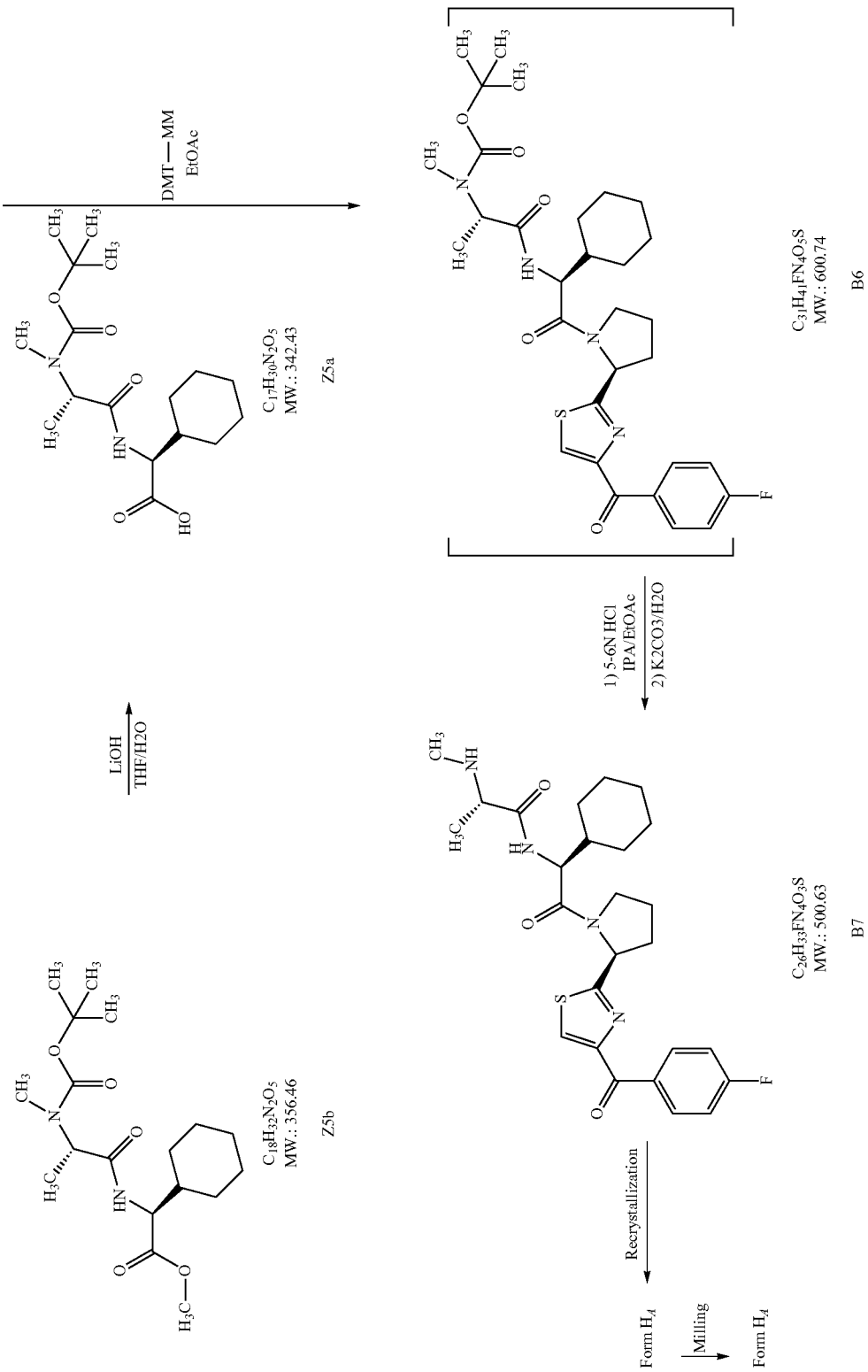

Form A

Form A can be obtained by equilibrating the hemihydrate Form $H_A$ in many organic solvent, e.g., acetone, acetonitrile, ethanol, etc.

Form A is an anhydrous crystalline. It is slightly hygroscopic. The maximum water uptake at 25° C. up to 95% RH is about 0.8%. The onset of melt of Form A by differential scanning calorimetry (DSC) is ~149° C.; it is followed by recrystallization into Form B upon further heating to ~155° C. The microscopic pictures show that Form A consists of aggregates of small needles.

Form A can be characterized by a powder x-ray diffraction pattern comprising three or more 2θ values selected from the group consisting of 5.3±0.2, 6.7±0.2, 9.1±0.2, 13.4±0.2, 13.6±0.2, 15.0±0.2, 15.3±0.2, 17.4±0.2, 18.2±0.2, 18.7±0.2, 18.9±0.2, 20.2±0.2, 21.3±0.2, 21.8±0.2, 23.0±0.2, 23.5±0.2, 24.6±0.2, and 27.6±0.2, at ambient temperature (i.e., at temperature from about 20° C. to 25° C.).

Form A can be characterized by a powder x-ray diffraction pattern comprising four or more 2θ values selected from the group consisting of 5.3±0.2, 6.7±0.2, 9.1±0.2, 13.4±0.2, 13.6±0.2, 15.0±0.2, 15.3±0.2, 17.4±0.2, 18.2±0.2, 18.7±0.2, 18.9±0.2, 20.2±0.2, 21.3±0.2, 21.8±0.2, 23.0±0.2, 23.5±0.2, 24.6±0.2, and 27.6±0.2, at ambient temperature (i.e., at temperature from about 20° C. to 25° C.).

Form A can be characterized by a powder x-ray diffraction pattern comprising five or more 2θ values selected from the group consisting of 5.3±0.2, 6.7±0.2, 9.1±0.2, 13.4±0.2, 13.6±0.2, 15.0±0.2, 15.3±0.2, 17.4±0.2, 18.2±0.2, 18.7±0.2, 18.9±0.2, 20.2±0.2, 21.3±0.2, 21.8±0.2, 23.0±0.2, 23.5±0.2, 24.6±0.2, and 27.6±0.2, at ambient temperature (i.e., at temperature from about 20° C. to 25° C.).

Form A can be characterized by a powder x-ray diffraction pattern comprising six or more 2θ values selected from the group consisting of 5.3±0.2, 6.7±0.2, 9.1±0.2, 13.4±0.2, 13.6±0.2, 15.0±0.2, 15.3±0.2, 17.4±0.2, 18.2±0.2, 18.7±0.2, 18.9±0.2, 20.2±0.2, 21.3±0.2, 21.8±0.2, 23.0±0.2, 23.5±0.2, 24.6±0.2, and 27.6±0.2, at ambient temperature (i.e., at temperature from about 20° C. to 25° C.).

Form A can be characterized by a powder x-ray diffraction pattern at ambient temperature (i.e., at temperature from about 20° C. to 25° C.), substantially in accordance with that shown in FIG. 1.

Figure 3:
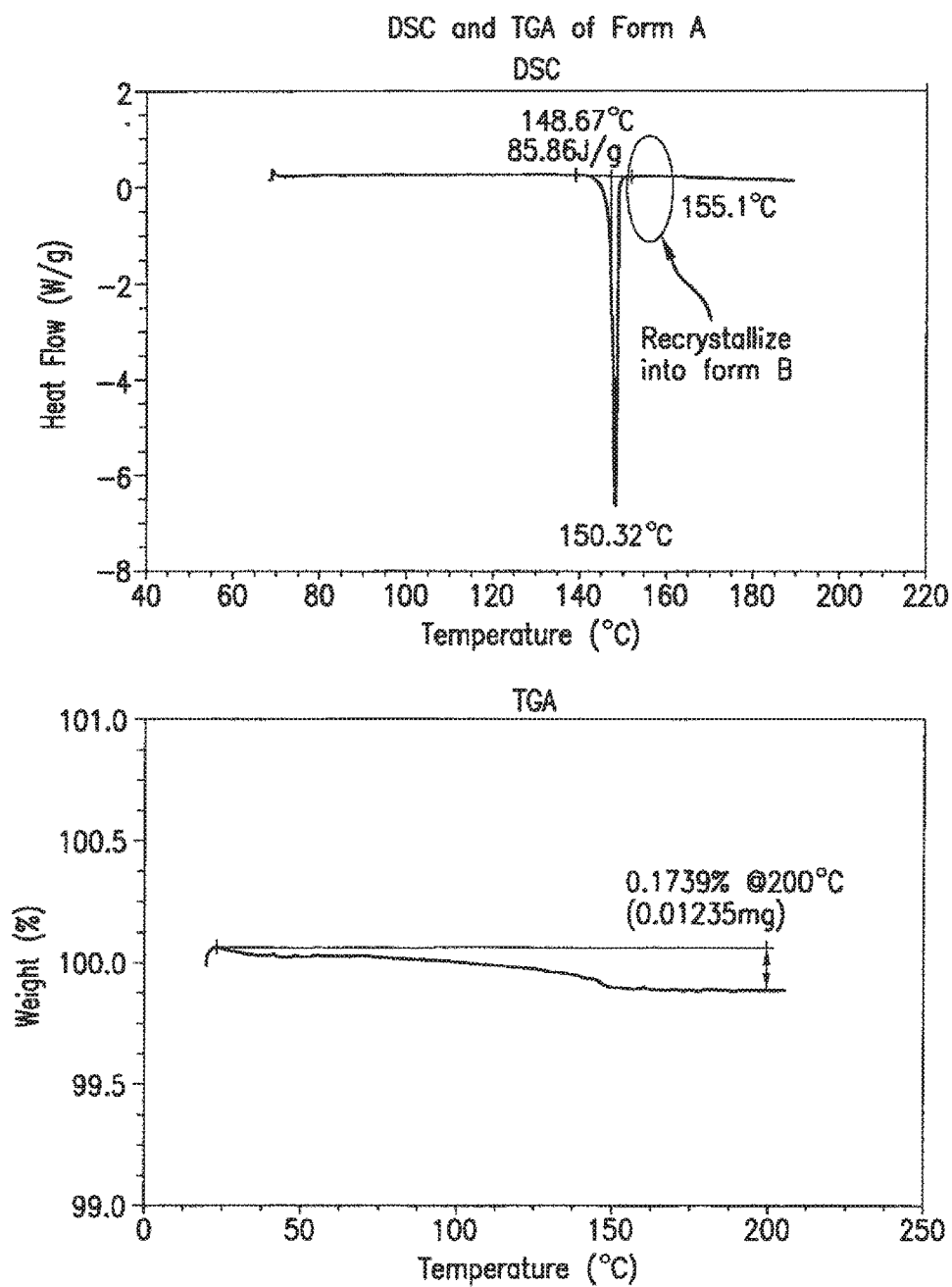
FIG. 3. illustrates the differential scanning calorimetry (DCS) pattern and thermogravimetric analysis pattern (TGA) of Form A of the compound of Formula (I).

Form A can be characterized by a differential scanning calorimetry (DSC) thermogram substantially in accordance with that shown in FIG. 3.

Form A can be characterized by a thermo gravimetric analysis (TGA) diagram substantially in accordance with that shown in FIG. 3.

Form B

Form B can be obtained by heating the hemihydrate Form $H_A$ above 100° C. over a period of time to remove the water completely, by equilibrating the hemihydrate Form $H_A$ in heptane at 50° C., or by cooling crystallization from methyl isobutyl ketone.

Form B is an anhydrous crystalline. It is slightly hygroscopic. The maximum water uptake at 25° C. up to 95% RH is about 0.5%. The onset of melt of Form B by DSC is ~153° C. Form B consists of long rods.

Form B can be characterized by a powder x-ray diffraction pattern comprising three or more 2θ values selected from the group consisting of 3.8±0.2, 7.7±0.2, 13.8±0.2, 14.6±0.2, 15.4±0.2, 17.6±0.2, 19.1±0.2, 19.2±0.2, 19.4±0.2, 20.0±0.2, 20.7±0.2, 20.9±0.2, and 22.8±0.2, at ambient temperature (i.e., at temperature from about 20° C. to 25° C.).

Form B can be characterized by a powder x-ray diffraction pattern comprising four or more 2θ values selected from the group consisting of 3.8±0.2, 7.7±0.2, 13.8±0.2, 14.6±0.2, 15.4±0.2, 17.6±0.2, 19.1±0.2, 19.2±0.2, 19.4±0.2, 20.0±0.2, 20.7±0.2, 20.9±0.2, and 22.8±0.2, at ambient temperature (i.e., at temperature from about 20° C. to 25° C.).

Form B can be characterized by a powder x-ray diffraction patter comprising five or more 2θ values selected from the group consisting of 3.8±0.2, 7.7±0.2, 13.8±0.2, 14.6±0.2, 15.4±0.2, 17.6±0.2, 19.1±0.2, 19.2±0.2. 19.4±0.2, 20.0±0.2, 20.7±0.2, 20.9±0.2, and 22.8±0.2, at ambient temperature (i.e., at temperature from about 20° C. to 25° C.).

Form B can be characterized by a powder x-ray diffraction pattern comprising six or more 2θ values selected from the group consisting of 3.8±0.2, 7.7±0.2, 13.8±0.2, 14.6±0.2, 15.4±0.2, 17.6±0.2, 19.1±0.2, 19.2±0.2, 19.4±0.2, 20.0±0.2, 20.7±0.2, 20.9±0.2, and 22.8±0.2, at ambient temperature (i.e., at temperature from about 20° C. to 25° C.).

Form B can be characterized by a powder x-ray diffraction pattern at ambient temperature (i.e., at temperature from about 20° C. to 25° C.), substantially in accordance with that shown in FIG. 1.

Figure 4:
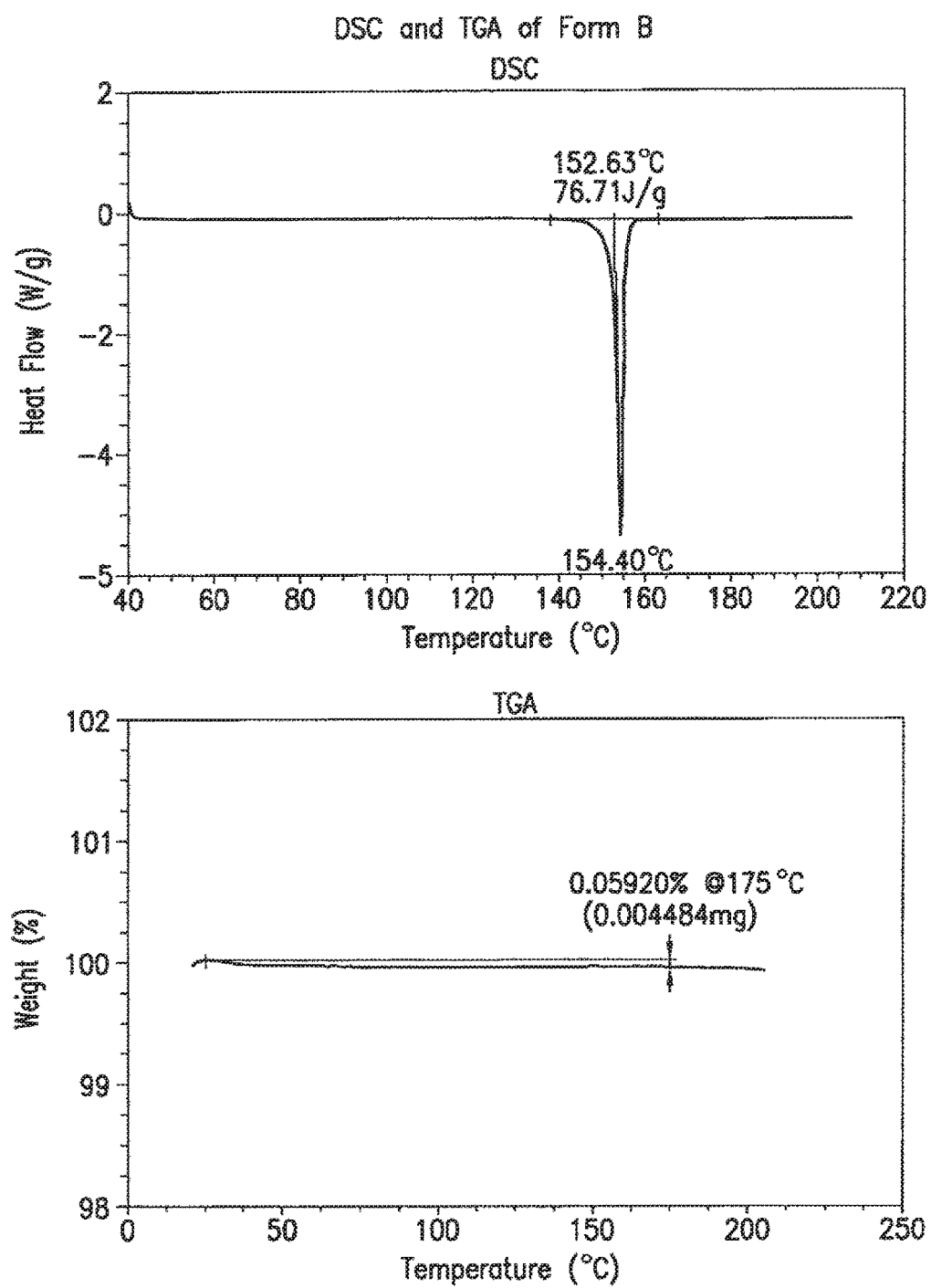
FIG. 4. illustrates the differential scanning calorimetry (DCS) pattern and thermogravimetric analysis pattern (TGA) of Form B of the compound of Formula (I).

Form B can be characterized by a differential scanning calorimetry (DSC) thermogram substantially in accordance with that shown in FIG. 4.

Form B can be characterized by a thermo gravimetric analysis (TGA) diagram substantially in accordance with that shown in FIG. 4.

Form C

Form C can be obtained by cooling crystallization from acetonitrile and then drying off the solvent after filtration.

Form C is an anhydrous crystalline. It is nonhygroscopic. The maximum water uptake at 25° C. up to 95% RH is less than 0.2%. The onset of melt of Form C by DSC is ~150° C.; it is followed by recrystallization into Form B upon further heating to ~155° C. Form C consists of long rods.

Form C can be characterized by a powder x-ray diffraction pattern comprising three or more 2θ values selected from the group consisting of 5.8±0.2, 7.7±0.2, 9.9±0.2, 13.0±0.2, 14.3±0.2, 15.5±0.2, 17.5±0.2, 19.4±0.2, 20.0±0.2, 22.9±0.2, and 24.3±0.2, at ambient temperature (i.e., at temperature from about 20° C. to 25° C.).

Form C can be characterized by a powder x-ray diffraction pattern comprising four or more 2θ values selected from the group consisting of 5.8±0.2, 7.7±0.2, 9.9±0.2, 13.0±0.2, 14.3±0.2, 15.5±0.2, 17.5±0.2, 19.4±0.2, 20.0±0.2, 22.9±0.2, and 24.3±0.2, at ambient temperature (i.e., at temperature from about 20° C. to 25° C.).

Form C can be characterized by a powder x-ray diffraction pattern comprising five or more 2θ values selected from the group consisting of 5.8±0.2, 7.7±0.2, 9.9±0.2, 13.0±0.2, 14.3±0.2, 15.5±0.2, 17.5±0.2, 19.4±0.2, 20.0±0.2, 22.9±0.2, and 24.3±0.2, at ambient temperature (i.e., at temperature from about 20° C. to 25° C.).

Form C can be characterized by a powder x-ray diffraction pattern comprising six or more 2θ values selected from the group consisting of 5.8±0.2, 7.7±0.2, 9.9±0.2, 13.0±0.2, 14.3±0.2, 15.5±0.2, 17.5±0.2, 19.4±0.2, 20.0±0.2, 22.9±0.2, and 24.3±0.2, at ambient temperature (i.e., at temperature from about 20° C. to 25° C.).

Form C can be characterized by a powder x-ray diffraction pattern at ambient temperature (i.e., at temperature from about 20° C. to 25° C.), substantially in accordance with that shown in FIG. 1.

Figure 5:
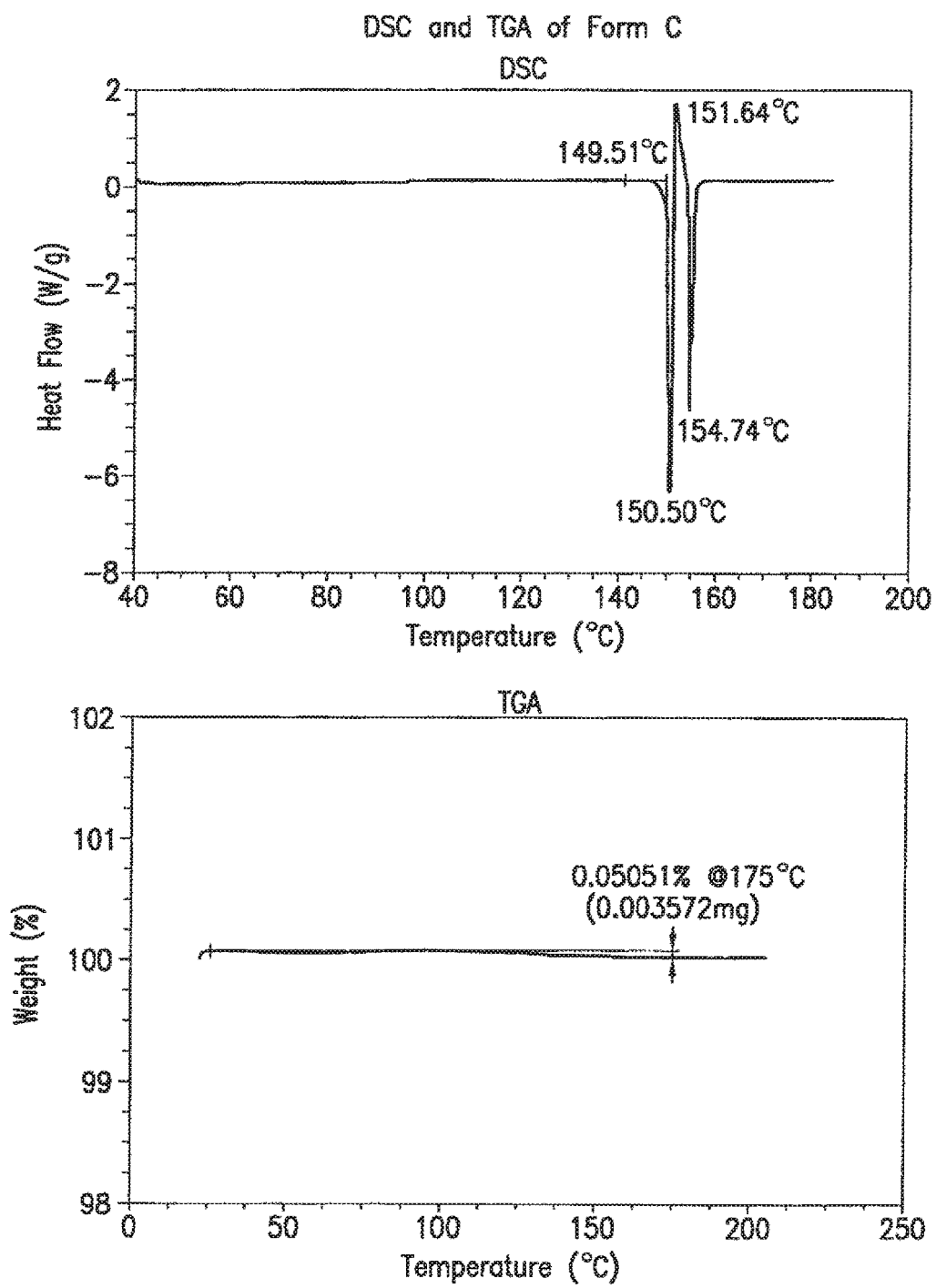
FIG. 5. illustrates the differential scanning calorimetry (DCS) pattern and thermogravimetric analysis pattern (TGA) of Form C of the compound of Formula (I).

Form C can be characterized by a differential scanning calorimetry (DSC) thermogram substantially in accordance with that shown in FIG. 5.

Form C can be characterized by a thermo gravimetric analysis (TGA) diagram substantially in accordance with that shown in FIG. 5.

Form D

Form D can be obtained by cooling crystallization from acetone and then drying off the solvent after filtration.

Form D is an anhydrous crystalline. It is slightly hygroscopic. The maximum water uptake at 25° C. up to 95% RH is less than 0.5%. The onset of melt of Form D by DSC is ~144° C.; it is followed by recrystallization into Form B upon further heating to ~155° C. Form D consists of bundles of thin rods.

Form D can be characterized by a powder x-ray diffraction pattern comprising three or more 2θ values selected from the group consisting of 6.5±0.2, 8.6±0.2, 11.3±0.2, 11.9±0.2, 13.1±0.2, 14.2±0.2, 15.1±0.2, 17.4±0.2, 19.6±0.2, 19.9±0.2, 20.4±0.2, 21.7±0.2, 25.6±0.2, and 31.7±0.2, at ambient temperature (i.e., at temperature from about 20° C. to 25° C.).

Form D can be characterized by a powder x-ray diffraction pattern comprising four or more 2θ values selected from the group consisting of 6.5±0.2, 8.6±0.2, 11.3±0.2, 11.9±0.2, 13.1±0.2, 14.2±0.2, 15.1±0.2, 17.4±0.2, 19.6±0.2, 19.9±0.2, 20.4±0.2, 21.7±0.2, 25.6±0.2, and 31.7±0.2, at ambient temperature (i.e., at temperature from about 20° C. to 25° C.).

Form D can be characterized by a powder x-ray diffraction pattern comprising five or more 2θ values selected from the group consisting of 6.5±0.2, 8.6±0.2, 11.3±0.2, 11.9±0.2, 13.1±0.2, 14.2±0.2, 15.1±0.2, 17.4±0.2, 19.6±0.2, 19.9±0.2, 20.4±0.2, 21.7±0.2, 25.6±0.2, and 31.7±0.2, at ambient temperature (i.e., at temperature from about 20° C. to 25° C.).

Form D can be characterized by a powder x-ray diffraction pattern comprising six or more 2θ values selected from the group consisting of 6.5±0.2, 8.6±0.2, 11.3±0.2, 11.9±0.2, 13.1±0.2, 14.2±0.2, 15.1±0.2, 17.4±0.2, 19.6±0.2, 19.9±0.2, 20.4±0.2, 21.7±0.2, 25.6±0.2, and 31.7±0.2, at ambient temperature (i.e., at temperature from about 20° C. to 25° C.).

Form D can be characterized by a powder x-ray diffraction pattern at ambient temperature (i.e., at temperature from about 20° C. to 25° C.), substantially in accordance with that shown in FIG. 1.

Figure 6:
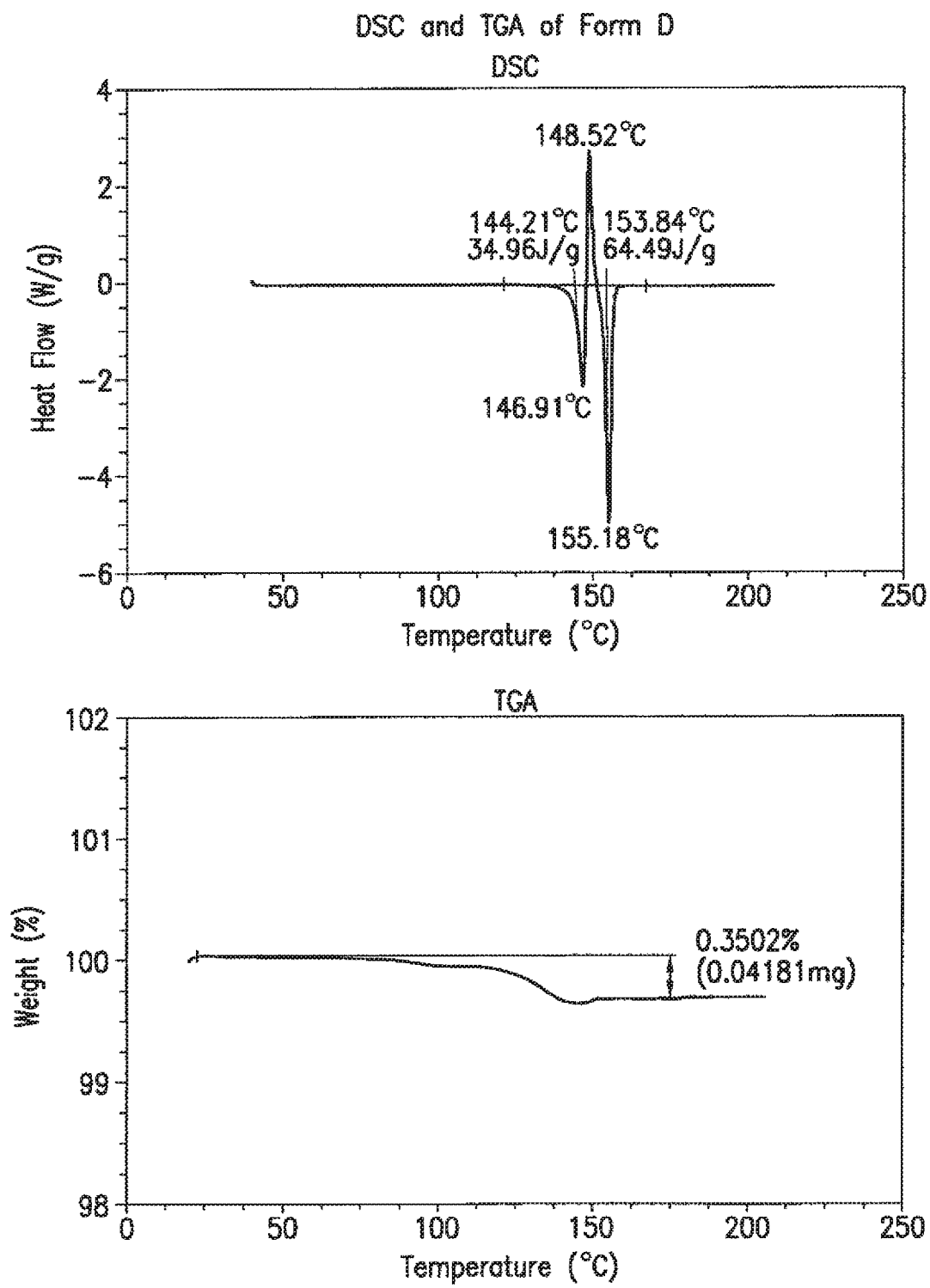
FIG. 6. illustrates the differential scanning calorimetry (DCS) pattern and thermogravimetric analysis pattern (TGA) of Form D of the compound of Formula (I).
Figure 7:
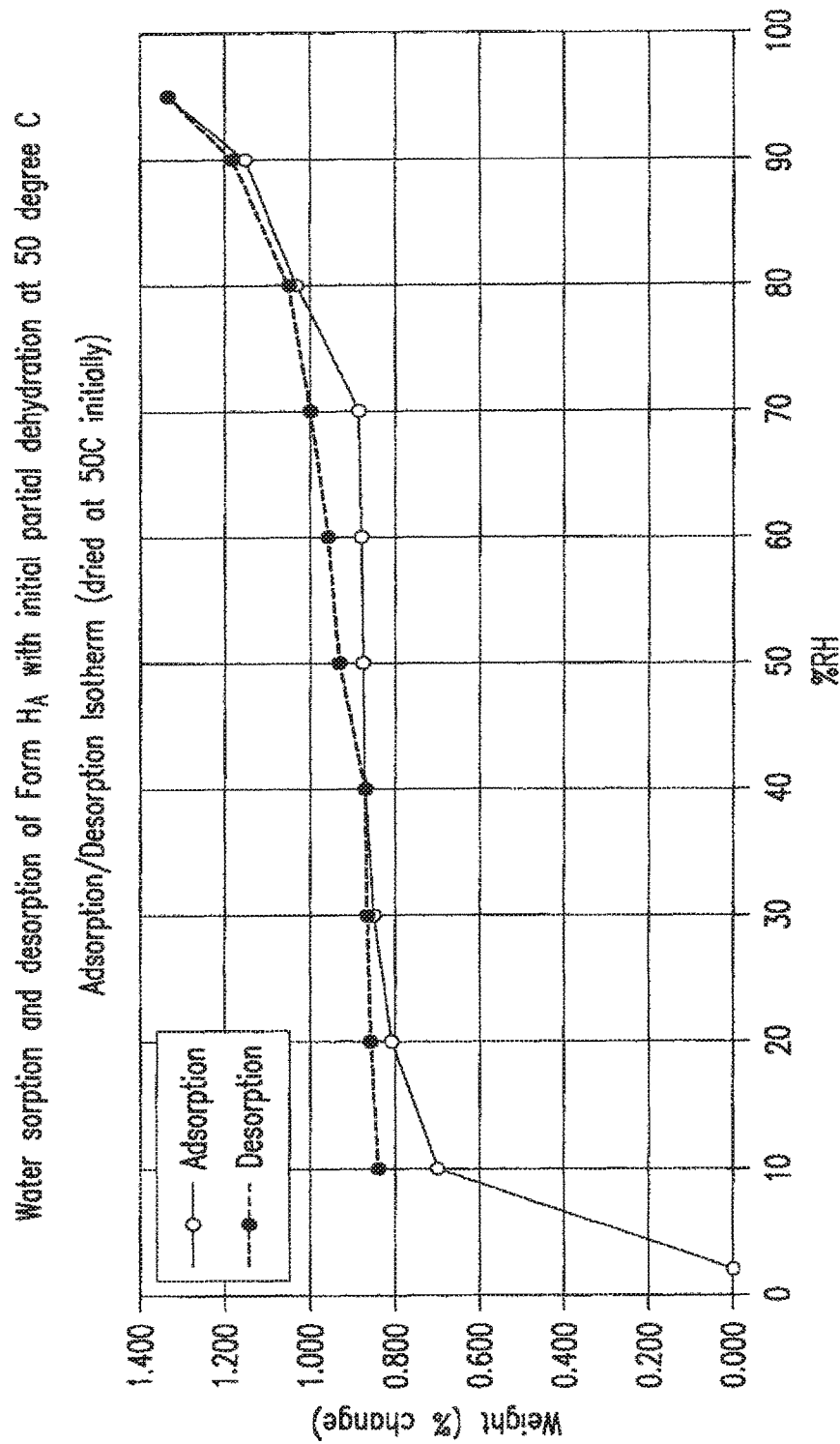
FIG. 7. illustrates the water sorption and desorption of Form $H_A$ of the compound of Formula (I), with initial partial dehydration at 50 degree C.
Figure 8:
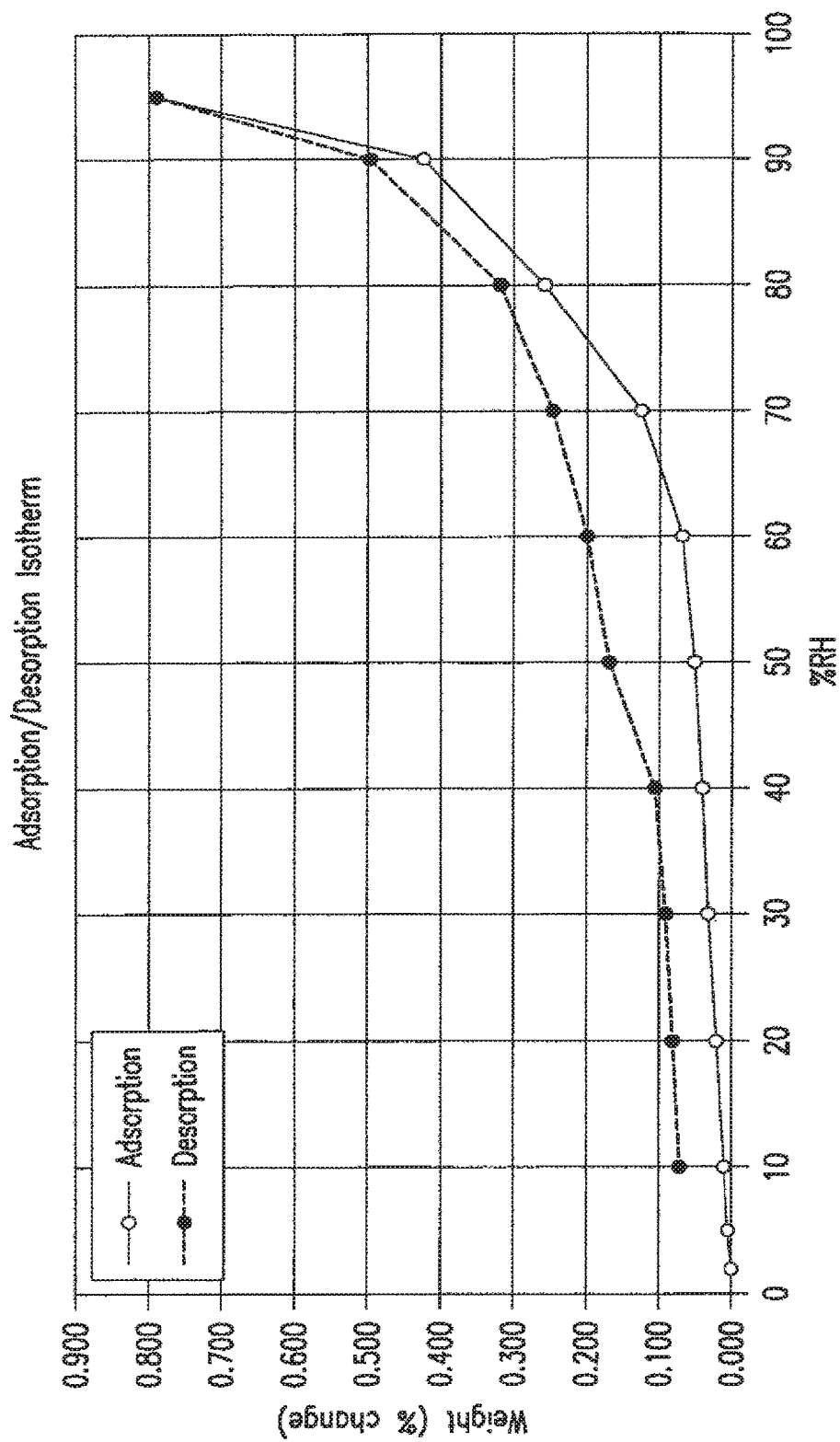
FIG. 8. illustrates the water sorption and desorption of Form A of the compound of Formula (I).
Figure 9:
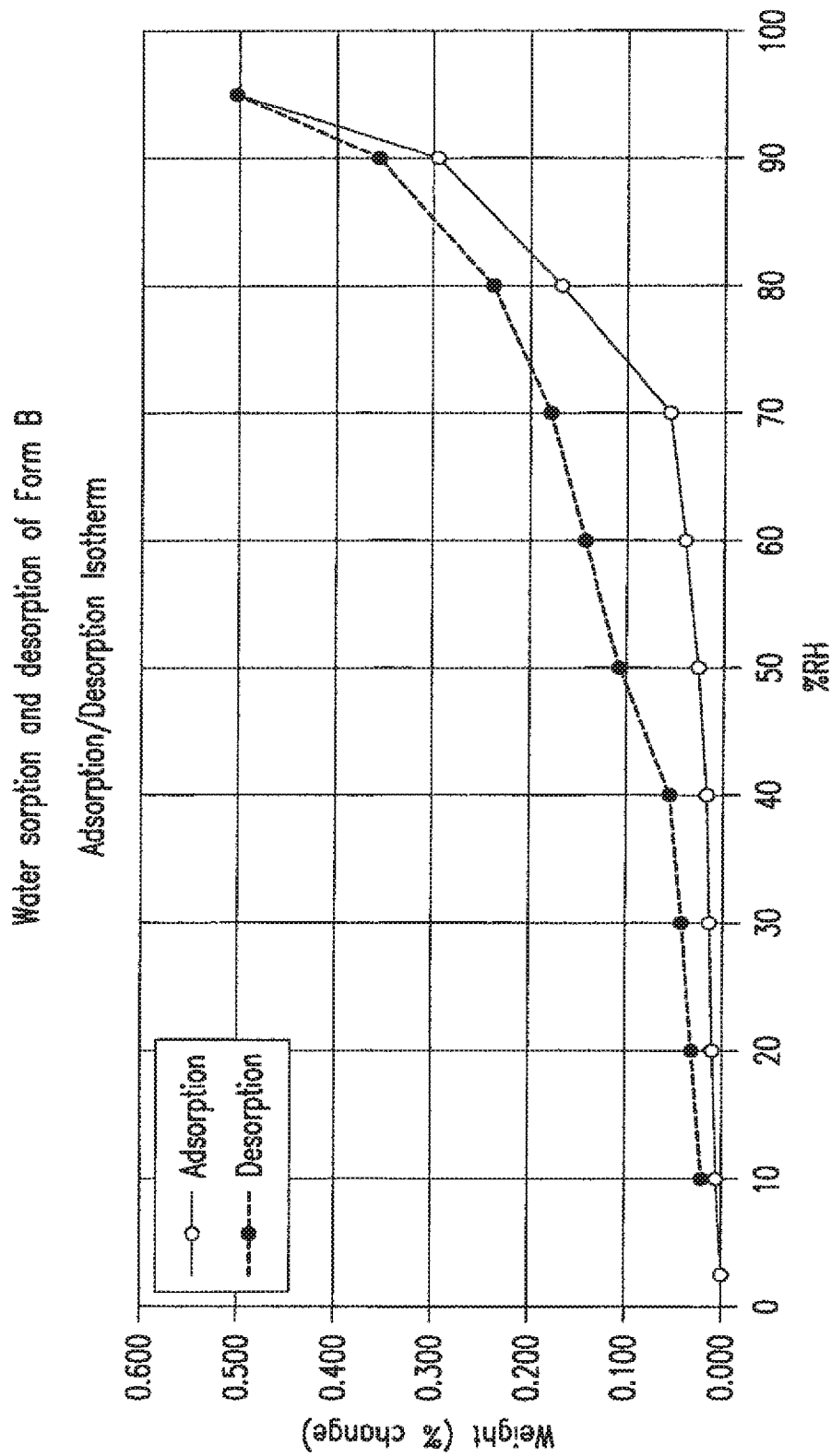
FIG. 9. illustrates the water sorption and desorption of Form B of the compound of Formula (I).
Figure 10:
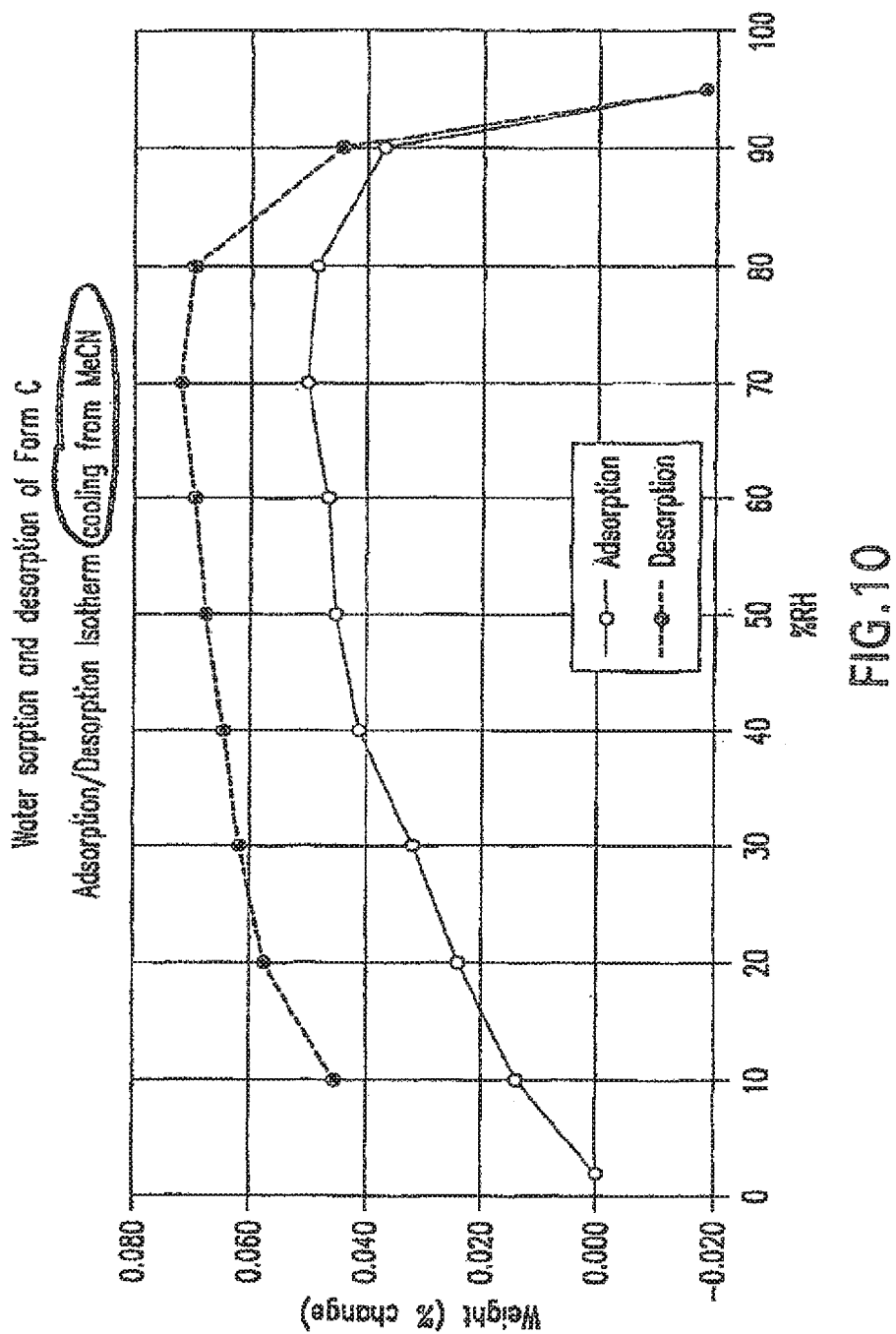
FIG. 10. illustrates the water sorption and desorption of Form C of the compound of Formula (I).
Figure 11:
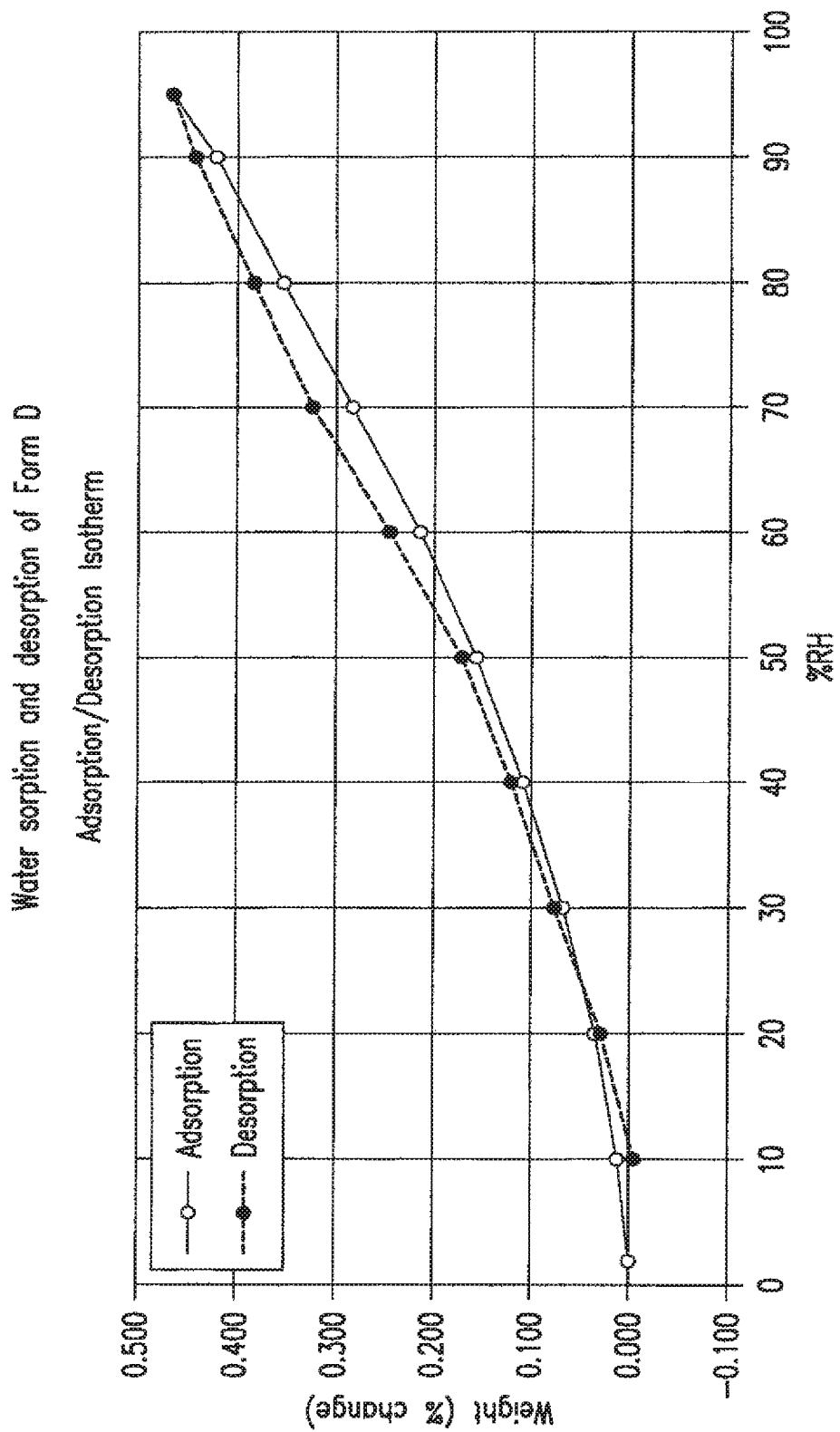
FIG. 11. illustrates the water sorption and desorption of Form D of the compound of Formula (I).
Figure 12:
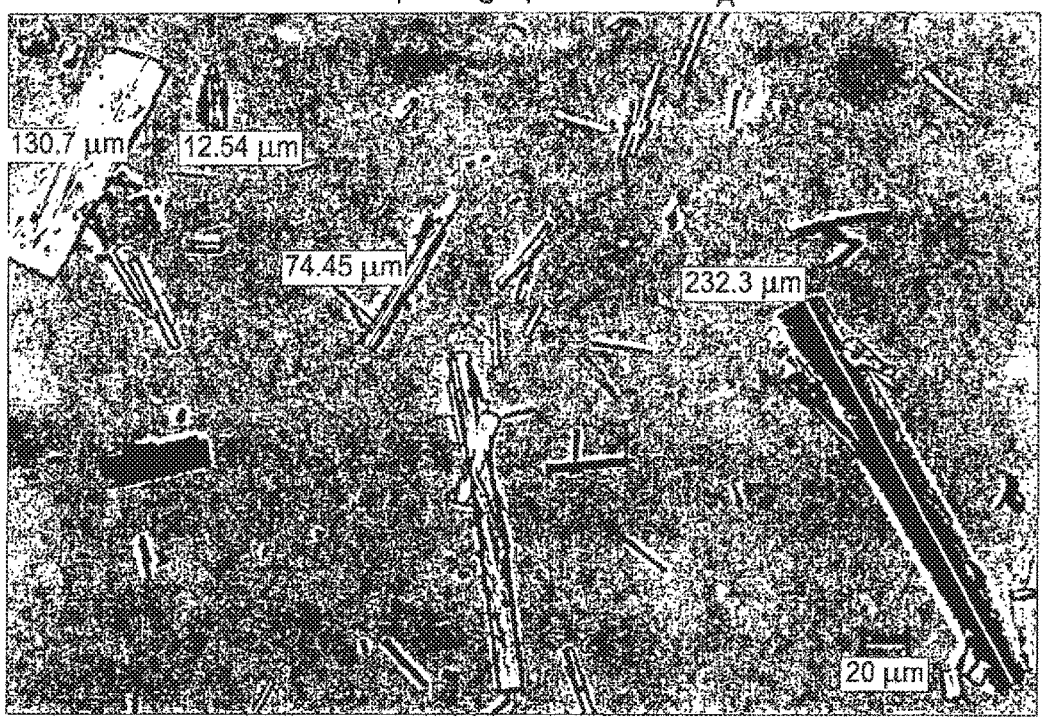
FIG. 12. illustrates the microphotograph of Form H$_A$ of the compound of Formula (I).
Figure 13:
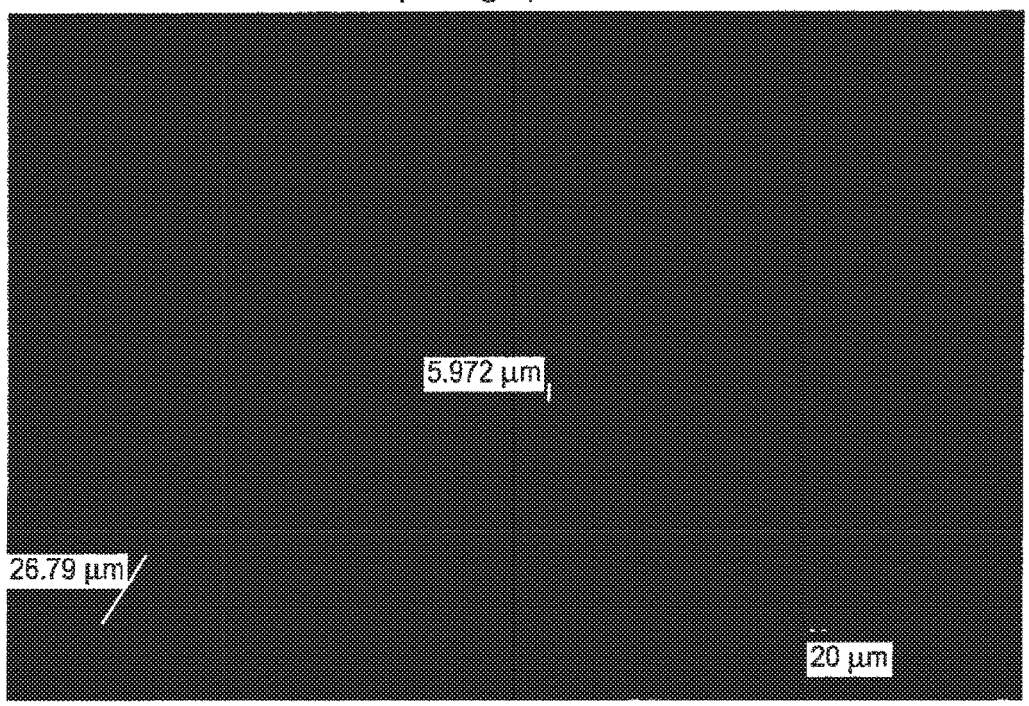
FIG. 13. illustrates the microphotograph of Form A of the compound of Formula (I).
Figure 14:
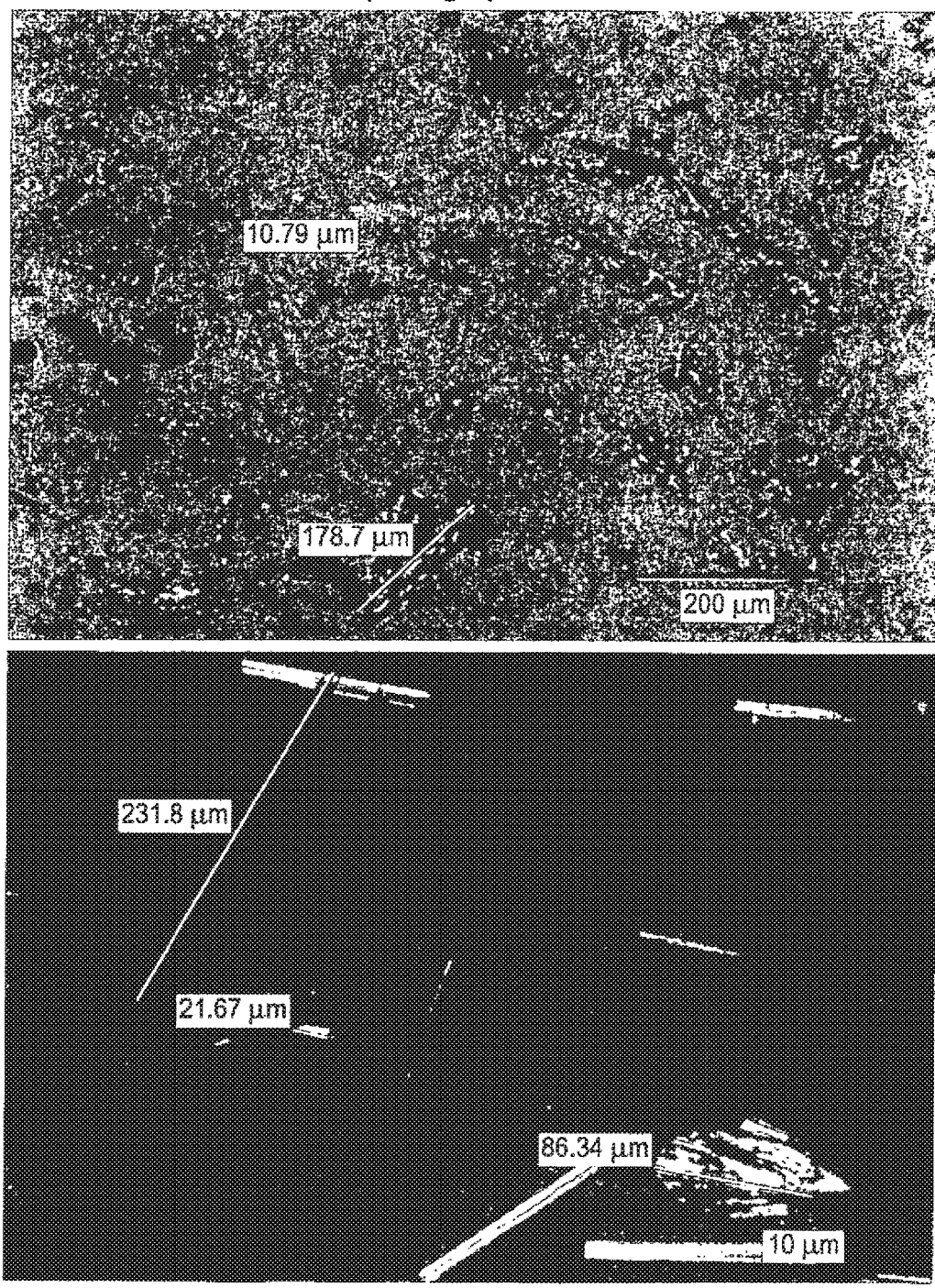
FIG. 14. illustrates the microphotograph of Form B of the compound of Formula (I).
Figure 15:
FIG. 15. illustrates the microphotograph of Form C of the compound of Formula (I).
Figure 16:
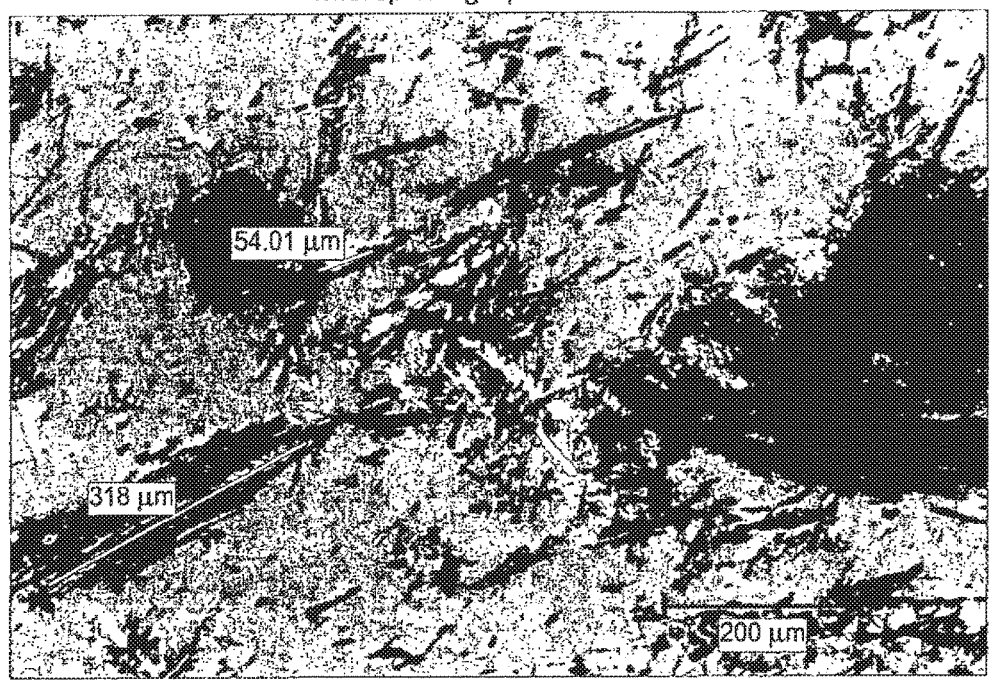
FIG. 16. illustrates the microphotograph of Form D of the compound of Formula (I).

Form D can be characterized by a differential scanning calorimetry (DSC) thermogram substantially in accordance with that shown in FIG. 6.

Form D can be characterized by a thermo gravimetric analysis (TGA) diagram substantially in accordance with that shown in FIG. 6.

Formulation of Compound of Formula (I)

(S)—N—((S)-1-cyclohexyl-2-{(S)-2-[4-(4-fluoro-benzoyl)-thiazol-2-yl]-pyrrolidin-1-yl})-2-oxo-ethyl)-2-methylamino-propionamide has low bulk density and poor flow capabilities. It is challenging to develop an oral formulation, especially at high dosage strength, i.e., the weight of the drug substance (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide (compound of Formula (I)) exceeds 100 mg. Typically, the amount of drug substance at high dosage strength is about 100 mg, 125 mg, 200 mg, 250 mg, 300 mg, 400 mg, 500 mg, or 600 mg.

The amount of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, its salt(s), and solvates (including hydrates) ranges from 5-600 mg in each oral dosage form. In one embodiment, it is from 10-100 mg. In another embodiment, it is from 100 to 600 mg. In yet another embodiment, it is from 200-600 mg. In still another embodiment, it is from 250-500 mg. Specifically, the amount could be 10, 20, 50, 100, 125, 150, 200, 250, 300, 400, 500 and 600 mg.

The manufacturing process for low dose including 10 mg and up to 50 mg consists of weighing of excipients and drug substance. This is followed by blending of drug substance with excipients like Microcrystalline cellulose, Mannitol, Dicalcium Phosphate, Spray dried Lactose, Polyvinyl pyrollidone XL, Starch, Colloidal silicone dioxide and magnesium stearate; preferably with Dicalcium phosphate, Microcrystalline cellulose, Polyvinyl pyrollidone XL and Colloidal silicone dioxide to obtain a pre-blend. The pre-blended is lubricated with magnesium stearate, and compressed to obtain cores which are film coated. The drug load varied from 7% up to 36%. But preferred from approximately 10% to approximately 18%.

The manufacturing process for the tablets containing more drug substance, including 250 mg and higher, preferable 300 mg or higher, 400 mg or higher, 500 mg or higher, starts with weighing of the excipients and drug substance. Once all excipients and drug substance are weighed, the drug substance is dry blended with microcrystalline cellulose, especially Avicel PH101 in a high shear mixer. The blended material is wetted preferably with PVP-K30 in a water solution. The wet mass is kneaded to obtain a granulate. The granulate is dried preferably is a fluidized bed dryer followed by screening. The screen granulate is lubricated to obtain a final blend which is compressed to obtained cores that are film coated.

The small particle and non-small particle forms of (S)—N—((S)-1-cyclohexyl-2-{(S)-2-[4-(4-fluoro-benzoyl)-thiazol-2-yl]-pyrrolidin-1-yl}-2-oxo-ethyl)-2-methylaminopropionamide can be present in crystalline or amorphous form, and hydrate forms or mixtures thereof. Salt forms of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide include HCl, tosic, methanesulfonic, benzenesulfonic, oxalic, ethanesulfonic, aspartic, maleic, and $H_2SO_4$.

As used herein, the term "pharmaceutically acceptable salts" refers to the nontoxic acid or alkaline earth metal salts of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide of the disclosure. These salts can be prepared in situ during the final isolation and purification of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, or by separately reacting the base or acid functions with a suitable organic or inorganic acid or base, respectively. Representative salts include, but are not limited to, the following: acetate, adipate, alginate, citrate, aspartate, benzoate, benzenesulfonate, a bile salt, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylpropionate, picrate, pivalate, propionate, succinate, sulfate, tartrate, thiocyanate, p-toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, and the like.

The formulation according to the disclosure may contain pharmaceutically acceptable excipients commonly used in pharmaceutical formulations, particularly those for oral administration.

In one embodiment according to the disclosure the formulation may be in the form of an oral solid dosage formulation comprising (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide or a salt thereof, with optionally one or more additional excipients. Examples of additional excipients include a disintegrant or super disintegrant, a filler, a glidant, or a lubricant. The (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide can be in small particle form.

Optionally, the formulation of the present disclosure can include surfactants. Surfactants suitable for the present disclosure include vitamin E TPGS, polysorbate 80, polysorbate 20, sodium lauryl sulfate, anionic surfactants of the alkyl sulfate type, for example sodium, potassium or magnesium n-dodecyl sulfate, n-tetradecyl sulfate, n-hexadecyl sulfate or n-octadecyl sulfate, of the alkyl ether sulfate type, for example sodium, potassium or magnesium n-dodecyloxyethyl sulfate, n-tetradecyloxyethyl sulfate, n-hexadecyloxyethyl sulfate or n-octadecyloxyethyl sulfate, or of the alkanesulfonate type, for example sodium, potassium or magnesium n-dodecanesulfonate, n-tetradecanesulfonate, n-hexadecanesulfonate or n-octadecanesulfonate, or non-ionic surfactants of the fatty acid polyhydroxy alcohol ester type, such as sorbitan monolaurate, monooleate, monostearate or monopalmitate, sorbitan tristearate or trioleate, polyoxyethylene adducts of fatty acid polyhydroxy alcohol esters, such as polyoxyethylene sorbitan monolaurate, monooleate, monostearate, monopalmitate, tristearate or trioleate, polyethylene glycol fatty acid esters, such as polyoxyethyl stearate, polyethylene glycol 400 stearate, polyethylene glycol 2000 stearate, especially ethylene oxide/propylene oxide block polymers of the PLURONICS® or SYNPERONIC® (ICI) type.

Vitamin E TPGS (d-alpha tocopheryl polyethylene glycol 1000 succinate) is normally a waxy substance at room temperature, which is difficult to process; however it can be made into a particulate form by freezing and then milling, which allows for direct blending of the vitamin E TPGS. A direct blending process is one that involves the dry processing of an excipient such as vitamin E TPGS and the active ingredient, in this case (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide. Dry processing means that the excipients are processed in a dry state and not melted, and moreover do not form a solid solution or solid dispersion. Vitamin E TPGS can be direct blended made by freezing and milling can be processed more easily, and can be present in the composition in an amounts up to about 20%, about 25%, or about 35%, or about 40%, or less than 50% (w/w). Dry processed vitamin E TPGS is present in the present disclosure in a powered or particulate form.

Surfactants for the present disclosure can be present in the formulation as about 0.5% to about 95%, about 1% to about 85%, and about 5% to about 75% (w/w) of the composition. In addition, compositions having about 5%, about 10%, about 15%, about 20%, about 25%, about 30%, about 35% and about 45% surfactant are envisioned.

Optionally, the formulation of the present disclosure can include acids. Acids for use with the present disclosure include any pharmaceutically acceptable acid, including organic acids such as succinic acid, tartaric acid, citric acid, acetic acid, propionic acid, maleic acid, malic acid, phthalic acid, methanesulfonic acid, toluenesulfonic acid, naphthalenesulfonic acid, camphorsulfonic acid, benzenesulfonic acid, lactic acid, butyric acid, hydroxymaleic acid, malonic acid, sorbic acid, glycolic acid, glucoronic acid, fumaric acid, mucic acid, gluconic acid, benzoic acid, oxalic acid, phenylacetic acid, salicyclic acid, sulphanilic acid, aspartic acid, glutamic acid, edetic acid, stearic acid, palmitic acid, oleic acid, lauric acid, pantothenic acid, tannic acid, valeric acid or ascorbic acid, and a polymeric acid such as methacrylic acid copolymer, EUDRAGIT E PO, EUDRAGIT L100-55, EUDRAGIT L-30 D-55, EUDRAGIT FS 30 D, EUDRAGIT NE 30 D, EUDRAGIT L100, EUDRAGIT S100, a poly-amino acid (e.g., poly-glutamic acid, poly-aspartic acid and combinations thereof), poly-nucleic acids, poly-acrylic acid, poly-galacturonic acid, and poly-vinyl sulfate or an anionic amino acid, such as polymer poly-glutamic acid or poly-aspartic acid. For purposes of describing the present disclosure, organic acids are understood to include polymeric acids. Acids can also include inorganic acids such as hydrochloric acid, phosphoric acid, phosphonic acid, phosphinic acid, boronic acid, hydrobromic acid, sulfuric acid, sulfamic acid, nitric acid, or sulfonic acid. The acid can be present as a buffer.

Acids for the present disclosure can be present in the formulation as about 2% to about 80%, about 2% to about 60%, and about 5% to about 40% (w/w) of the composition. In addition, compositions having about 10%, about 20%, about 25%, about 35%, about 40%, and about 45% acid are envisioned.

Optionally, the formulation of the present disclosure can include antioxidant. Non-limiting examples of antioxidants include sodium sulfite, sodium bisulfite, sodium metabisulphite, sodium metabisulfite, ascorbic acid, thioglycerol, thiosorbitol, thiocarbamide, sodium thiosulphate, thioacetic acid, cysteine, methionine, butylated hydroxytoluene (BHT), butylated hydroxyanisole (BHA), ascorbyl palmitate, hydroquinone, propyl gallate, nordihydroguaiaretic acid, Vitamin E (alpha-tocopherol) and lecithin. The preferred antioxidants are micronized propyl gallate, micronized BHA, micronized BHT, Vitamin E, ascorbic acid, sodium thiosulphate, and cysteine. The concentration of antioxidant is from 1-3% (w/w).

Disintegrants for use with the present disclosure can include traditional disintegrants, such as starch, alginic acid or amberlite resins; also included are super disintegrants, such as crospovidone, sodium starch glycolate, croscarmellose sodium, and soy polysaccharide. The term "super disintegrant" is a term well known in the art and denotes a disintegrant that is effective in lower concentrations in comparison to starch, generally at 2 to 4% w/w.

Glidants for use with the present disclosure include silicon dioxide, such as colloidal silicon dioxide (fumed silica) and talc.

In one embodiment, the formulation of the present disclosure are made by wet granulation process, comprising compound of Formula (I) and excipients in the following range:

|  | Component | Percentage (%) |
|---|---|---|
| Internal granular | Compound of Formula (I) | 40-60 |
|  | Binder/Filler (e.g., Avicel pH 101) | 15.0-37.4 |
|  | Binder (e.g., Polyvinylpyrrolidone (K 30).001) | 3.0-10.0 |
| Extra granular | Binder/Filler (e.g., Avicel pH 102) | 0.0-22.4 |
|  | Disintegrant (e.g., Crospovidone.001) | 2.0-8.0 |
|  | Glidant (e.g., Aerosil 200 PH.001) | 0.5-1.0 |
|  | Lubricant (e.g., Magnesium Stearate PH.001) | 0.5-1.5 |

In another embodiment, the formulation of the present disclosure are made by wet granulation process, comprising compound of Formula (I) and excipients in the following range:

|  | Component | Percentage (%) |
|---|---|---|
| Internal granular | Compound of Formula (I) | 50-70 |
|  | Binder/Filler (e.g., Avicel pH 101/105) | 10.00-27.23 |
|  | Binder (e.g., Polyvinylpyrrolidone (K 30).001) | 3.0-10.0 |
| Extra granular | Binder/Filler (e.g., Avicel pH 102) | 0.00-17.23 |
|  | Disintegrant (e.g., Crospovidone.001) | 2.0-8.0 |
|  | Glidant (e.g., Aerosil 200 PH.001) | 0.5-1.0 |
|  | Lubricant (e.g., Magnesium Stearate PH.001) | 0.5-1.5 |

In another embodiment, the formulation of the present disclosure are made by wet granulation process, comprising compound of Formula (I) and excipients in the following range:

|  | Component | Percentage (%) |
|---|---|---|
| Internal granular | Compound of Formula (I) | 60-80 |
|  | Binder/Filler (e.g., Avicel pH 101/105) | 10.0-23.43 |
|  | Binder (e.g., Polyvinylpyrrolidone (K 30).001) | 3.0-10.0 |

-continued

|  | Component | Percentage (%) |
|---|---|---|
| Extra granular | Binder/Filler (e.g., Avicel pH 102) | 0.0-13.43 |
|  | Disintegrant (e.g., Crospovidone.001) | 2.0-8.0 |
|  | Glidant (e.g., Aerosil 200 PH.001) | 0.50-1.0 |
|  | Lubricant (e.g., Magnesium Stearate PH.001) | 0.5-1.5 |

Fillers: MCC, including Avicel pH101, 102, 105, 201 . . . etc; Celous®; Sugars, such as Lactose, mannitol, dextrose, starch, etc; or other inorganic fillers, such as Di-calcium hydrogen phosphate, Tri-calcium phosphate, calcium sulfate, etc. can be used.

Various solvents can be used for the wet granulation process. Non-limiting examples of solvent include water, alcohols (e.g. ethyl alcohol, isopropanol) or mixture of thereof, especially mixtures of water and alcohol(s).

In one embodiment, the formulation of the present disclosure are made by dry granulation process, comprising compound of Formula (I) and excipients in the following range:

|  | Component | Percentage (%) |
|---|---|---|
| Internal granular | Compound of Formula (I) | 40-60 |
|  | Binder/Filler (e.g., Avicel pH 101) | 15.0-37.4 |
|  | Disintegrant (e.g., Crospovidone) | 1.0-5.0 |
| Extra granular | Binder/Filler (e.g., Avicel pH 102) | 0.0-22.4 |
|  | Disintegrant (e.g., Crospovidone.001) | 2.0-5.0 |
|  | Glidant (e.g., Aerosil 200 PH.001) | 0.5-1.0 |
|  | Lubricant (e.g., Magnesium Stearate PH.001) | 0.5-1.5 |

In another embodiment, the formulation of the present disclosure are made by dry granulation process, comprising compound of Formula (I) and excipients in the following range.

|  | Component | Percentage (%) |
|---|---|---|
| Internal granular | Compound of Formula (I) | 50-70 |
|  | Filler/binder (Such as Avicel pH 101/105) | 10.00-27.23 |
|  | Disintegrant (e.g., Crospovidone.001) | 1.0-5.0 |
| Extra granular | Binder/Filler (e.g., Avicel pH 102) | 0.0-17.23 |
|  | Disintegrant (e.g., Crospovidone.001) | 2.0-5.0 |
|  | Glidant (e.g., Aerosil 200 PH.001) | 0.5-1.0 |
|  | Lubricant (e.g., Magnesium Stearate PH.001) | 0.5-1.5 |

In another embodiment, the formulation of the present disclosure are made by dry granulation process, comprising compound of Formula (I) and excipients in the following range:

| | Component | Percentage (%) |
|---|---|---|
| Internal granular | Compound of Formula (I) | 60-80 |
| | Binder/Filler (e.g., Avicel pH 101/105) | 10.0-23.43 |
| | Disintegrant (e.g., Crospovidone) | 1.0-5.0 |
| Extra granular | Binder/Filler (e.g., Avicel pH 102) | 0.0-13.43 |
| | Disintegrant (e.g., Crospovidone.001) | 2.0-5.0 |
| | Glidant (e.g., Aerosil 200 PH.001) | 0.5-1.0 |
| | Lubricant (e.g., Magnesium Stearate PH.001) | 0.5-1.5 |

Fillers: MCC, including Avicel pH101, 102, 105, 201 . . . etc; Celous®; Sugars, such as Lactose, mannitol, dextrose, starch, etc; or other inorganic fillers, such as Di-calcium hydrogen phosphate, Tri-calcium phosphate, calcium sulfate, etc can be used.

Any crystalline forms of compound of Formula (I), its salts, or solvates (including hydrates), including but limited to Forms HA, A, B, C, and D, or mixtures thereof can be used to make the formulations of the present disclosure. may or may not under go changes of form during the process of the formulation manufacture.

An example of a lubricant that can be used with the present disclosure is magnesium stearate, stearic acid calcium stearate, talc, hydrogenated vegetable oil, gylceryl behenete, sodium stearyl fumarate, PEG 4000/000, sodium lauryl sulphate, isoleucine, sodium benzoate, or fumed silica.

Fillers can be used with the present disclosure, microcrystalline cellulose (MCC), for example of the AVICEL® type (FMC Corp.), for example of the types AVICEL® PH101, 102, 105, RC581 or RC 591, EMCOCEL® type (Mendell Corp.) or ELCEMA type (Degussa), Co-precipitated MCC such Silicified MCC (Prosolv-JRS pharma), co processed such as Ludipress (BASF) that consists of Lactose and Kollidon® 30 and Kollidon® CL; carbohydrates, such as sugars, sugar alcohols, starches or starch derivatives, for example sucrose, lactose, dextrose, saccharose, glucose, sorbitol, mannitol, xylitol, potato starch, maize starch, rice starch, wheat starch or amylopectin, tricalcium phosphate, calcium hydrogen phosphate, calcium sulfate, dibasic calcium phosphates, magnesium oxide or magnesium trisilicate.

Suitable binders that can be used with the present disclosure include gelatin, tragacanth, agar, alginic acid, sodium alginate, acacia, cellulose ethers, for example methylcellulose, carboxymethylcellulose or hydroxypropylmethylcellulose, hydroxypropylcellulose, methylcellulose polyethylene glycols or ethylene oxide homopolymers, especially having a degree of polymerization of approximately from $2.0 \times 10^3$ to $1.0 \times 10^5$ and an approximate molecular weight of about from $1.0 \times 10^5$ to $5.0 \times 10^6$, for example excipients known by the name POLYOX® (Union Carbide), polyvinylpyrrolidone or povidones, especially having a mean molecular weight of approximately 1000 and a degree of polymerization of approximately from 500 to 2500, and also agar or gelatin.

Suitable polymers that can be used for film coating can be hydroxypropylmethylcellulose, Hydroxypropyl methylcellulose phthalate Ethylcellulose, methylcellulose, polyvinyl alcohol based, polyvinyl acetate based, or acrylate based such as Eudragit® EPO, Eudragit® RL and RS30, Eudragit® L30D (Evonik).

The formulation of the present disclosure can be manufactured with a standard process, such as direct blending, direct compression, granulation, solvent granulation, wet granulation, fluid-bed granulation, (hot) melt granulation, dry granulation, roller compaction, slugging, freeze dried tabletting, wet or dry aggregation, and extrusion and spheronization.

In one embodiment, the present disclosure is formulated as a capsule, such as hard gelatin capsule or a soft elastic capsule. Alternatively, the present disclosure is in the form of a tablet or a pill. In these solid oral formulations the amount of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide can be present in the ranges of 1-900 mg, 2.5-600 mg, 2.5-300 mg or 2.5-100 mg with preferred examples including 10 mg, 50 mg, 100 mg, 200 mg, 250 mg, 300 mg, 400 mg, 500 mg and 600 mg.

The solid oral formulations of the present disclosure can be administered to treat diseases related to the inhibition of Apoptosis Protein. Apoptosis Protein protects cancer cells from apoptotic cell death.

The exact dosage regimen of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide in the formulations of the present disclosure can be determined by one of skill in art upon consideration of the condition and requirements of the patient. For example, the present disclosure could be administered daily, every other day or weekly.

The present invention(s) is further described in the following example. The following non-limiting examples illustrate the invention(s) and are not to be construed as limiting the scope of the appended claims.

Example 1

The below Table 1 illustrates tablet with 10 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide.

TABLE 1

Composition of 10 mg Film coated tablet (FTC)

| Component | Core Composition per unit [%] | Core Composition per unit [mg/unit] | Function |
|---|---|---|---|
| (S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide* | 3.57 | 10.177 | Active ingredient |
| Dicalcium Phosphate | 42.11 | 120.0 | Filler |
| Microcrystalline Cellulose | 49.54 | 141.193 | Filler/Binder |
| Polyvinylpolypyrrolidone XL | 2.28 | 6.5 | Disintegrant |
| Aerosil 200 | 1.0 | 2.85 | Glidant |
| Magnesium Stearate | 1.5 | 4.28 | Lubricant |
| Weight of core | | 285 | |
| Opadry premix white | | 10 | Film forming agent |
| Purified water[1] | q.s. | q.s. | Solvent |
| Weight of Formulation | | 295 | |

Figure 17:
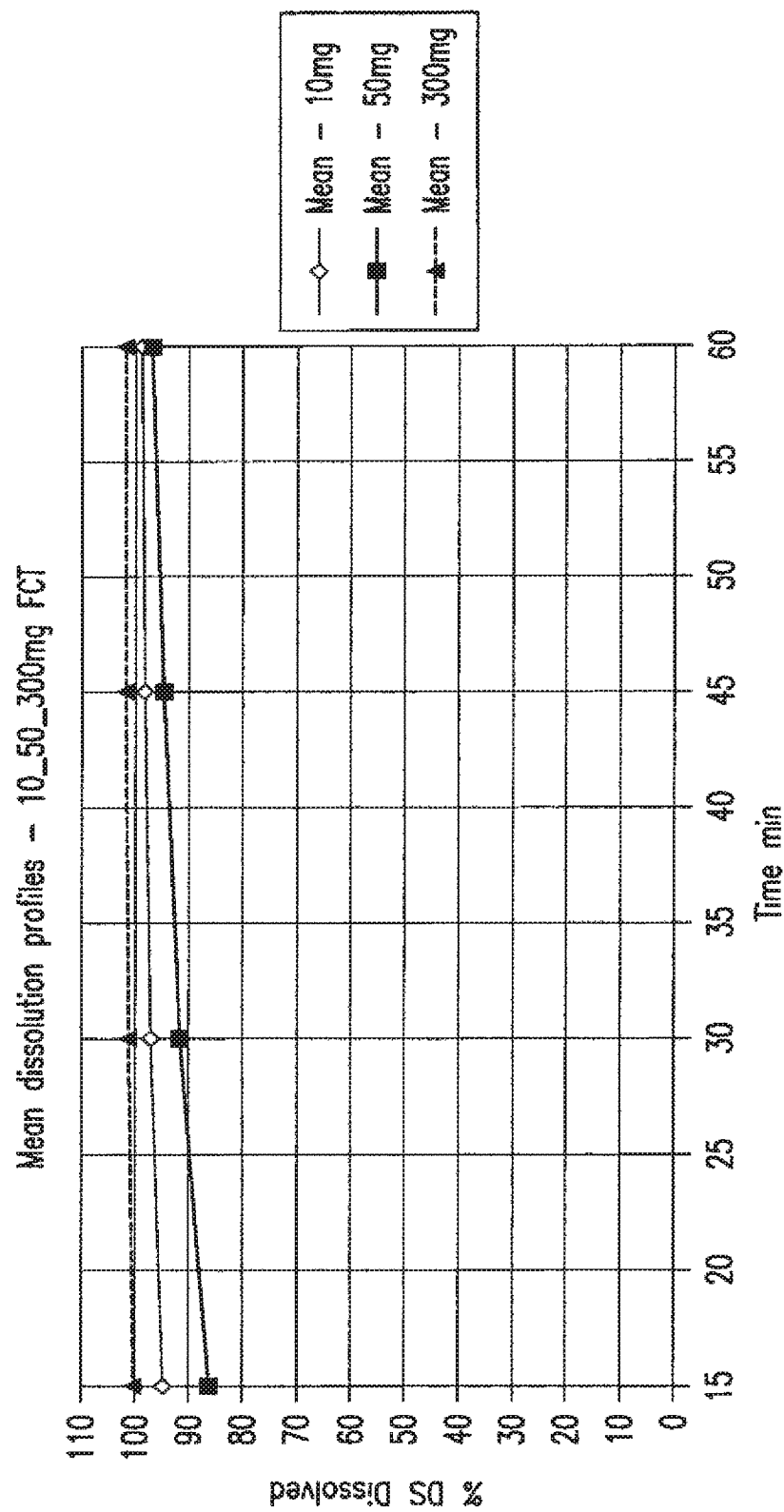
FIG. 17. illustrates the dissolution profile of the 10 mg tablet formulation, 50 mg tablet formulation, and 300 mg tablet formulation made according to Examples 1-3.

*(S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is a hemihydrate containing 1.77% stoichiometric water. (Purity 98.23% on anhydrous basis)
[1]Removed during coating The Mean dissolution of profile is shown in FIG. 17.

Direct compression method is employed for the manufacture of 10 mg tablets using directly compressible excipients like Microcrystalline cellulose, Mannitol, Dicalcium Phosphate and Spray dried Lactose in combination with disintegrants (like Polyvinyl pyrollidone XL, Starch), lubricant (Magnesium Stearate) and a glidant (Colloidal Silicone Dioxide). The drug load varies from 7% up to 36%.

High ejection forces are observed with formulations containing Mannitol. This problem is resolved by replacing Mannitol with Dicalcium phosphate or Lactose and decreasing the drug load. In some instances sticking and high variation in compression force are observed, normally, associated with inadequate lubrication and bad flow. This is resolved by decreasing the drug load.

Example 2

The below Table 2 illustrates tablet with 50 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methyl-amino-propionamide.

TABLE 2

Composition of 50 mg Film coated tablet (FTC)

| Component | Core Composition per unit [%] | Core Composition per unit [mg/unit] | Function |
|---|---|---|---|
| (S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide* | 17.854 | 50.885 | Active ingredient |
| Dicalcium Phosphate | 35.087 | 100.0 | Filler |
| Microcrystalline Cellulose | 42.265 | 120.455 | Filler/Binder |
| Polyvinylpolypyrrolidone XL | 2.281 | 6.50 | Disintegrant |
| Aerosil 200 | 1.004 | 2.86 | Glidant |
| Magnesium Stearate | 1.509 | 4.30 | Lubricant |
| Weight of core |  | 285 |  |
| Opadry premix white |  | 10 | Film forming agent |
| Purified water[1] | q.s. | q.s. | Solvent |
| Weight of Formulation |  | 295 |  |

*(S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is a hemihydrate containing 1.77% stoichiometric water. (Purity 98.23% on anhydrous basis)
[1]Removed during coating Direct compression method is employed for the manufacture of the 50 mg tablets using directly compressible excipients like Microcrystalline cellulose, Mannitol, Dicalcium Phosphate and Spray dried Lactose in combination with disintegrants (like Polyvinyl pyrollidone XL, Starch), lubricant (Magnesium Stearate) and a glidant (Colloidal Silicone Dioxide). The drug load varies from 7% up to 36%.

High ejection forces are observed with formulations containing Mannitol. This problem is resolved by replacing Mannitol with Dicalcium phosphate or Lactose and decreasing the drug load. In some instances sticking and high variation in compression force are observed, which are normally associated with inadequate lubrication and bad flow. This is resolved by decreasing the drug load.

The Mean dissolution of profile is shown in FIG. 17.

Example 3

Table 3 illustrates tablets with 300 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide.

TABLE 3

Composition of 300 mg Film coated tablet (FTC)

| Component | Core Composition per unit [%] | Core Composition per unit [mg/unit] | Function |
|---|---|---|---|
| (S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide* | 50.87 | 305.2 | Active ingredient |
| Avicel PH101 | 36.55 | 219.3 | Filler/Binder |
| Polyvinylpryrrolidone K30 PH | 5.50 | 33.00 | Binder |
| Purified water[1] | q.s. | q.s. | Granulating solvent |
| Polyvinylpolypyrrolidone XL | 5.00 | 30.00 | Disintegrant |
| Aerosil 200 | 0.58 | 3.500 | Glidant |
| Magnesium Stearate | 1.50 | 9.000 | Lubricant |
| Weight of core |  | 600 |  |
| Opadry premix white |  | 19 | Film forming agent |
| Purified water[2] | q.s. | q.s. | Solvent |
| Weight of Formulation |  | 619 |  |

*(S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is a hemihydrate containing 1.77% stoichiometric water. (Purity 98.23% on anhydrous basis)
[1]Removed during coating The Mean dissolution of profile is shown in FIG. 17.

Based on the experience from 10 and 50 mg formulation development, several compaction simulation trials on a single punch machine are carried out in an attempt to develop higher strength (e.g. 250 mg) by simulating roller compaction process. Several trials are done, to assess the processability, using combination of excipients like microcrystalline cellulose, pregelatinized starch, dicalcium phosphate and mannitol as fillers and hydroxypropyl cellulose, Kollidon VA64, as binders. Several issues like bad flow, sticking poor compaction are observed even at drug load of about 30%. These problems could not be solved by qualitative or quantitative variations of the excipients. It is thought that milled drug substance, with greater surface area (hence greater bonding area) would provide stronger compacts/granulate proving granules on milling that can be processed; however no significant improvement is seen. These compaction simulation results are unexpected. No attempt was made to reduce the drug load below 30% as that would have increased the size of tablet considerably; inconvenient for the subject especially when intake of multiple tablets is planned in the clinical study.

The technical manufacturing problems are successfully solved and higher drug load (greater than 40% w/w, greater than 50% w/w, greater than 60% w/w, greater than 70% w/w, or greater than 80% w/w) is obtained by using the wet granulation and/or the dry granulation processes. In a wet granulation method, the high dosage strength with a high drug load (e.g., 50% w/w) is possible with specifically selected and adjusted conventional excipients and granulating solvent.

Example 4

The below Table 4 illustrates tablet with 500 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide. The tablet might be film coated.

TABLE 4

Composition of 500 mg Tablet

| Component | Core Composition per unit [%] | Core Composition per unit [mg/unit] | Function |
|---|---|---|---|
| (S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide* | 50.89 | 508.9 | Active ingredient |
| Avicel PH101 | 36.53 | 365.27 | Filler/Binder |
| Polyvinylpryrrolidone K30 PH | 5.50 | 55.0 | Binder |
| Purified water[1] | q.s. | q.s. | Granulating solvent |
| Polyvinylpolypyrrolidone XL | 5.00 | 50.0 | Disintegrant |
| Aerosil 200 | 0.58 | 5.83 | Glidant |
| Magnesium Stearate | 1.50 | 15.0 | Lubricant |
| Weight of core | | 1000 | |

Figure 18:
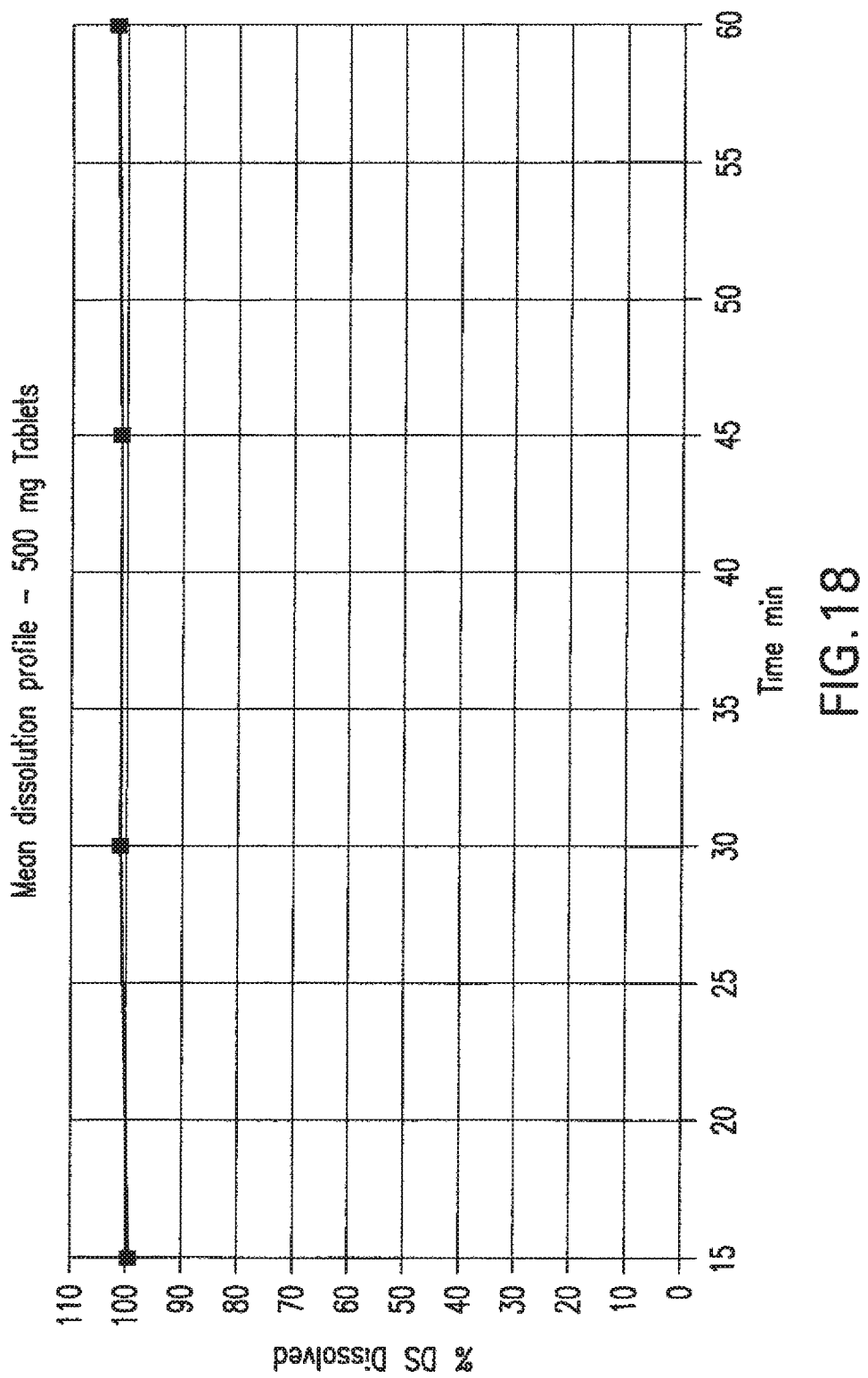
FIG. 18. illustrates the dissolution profile of the 500 mg tablet formulation made according toe Example 4.

*(S)-N-((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is a hemihydrate containing 1.77% stoichiometric water. (Purity 98.23% on anhydrous basis)
[1] Removed during coating The Mean dissolution of profile is shown in FIG. 18.

Example 5

Figure 19:
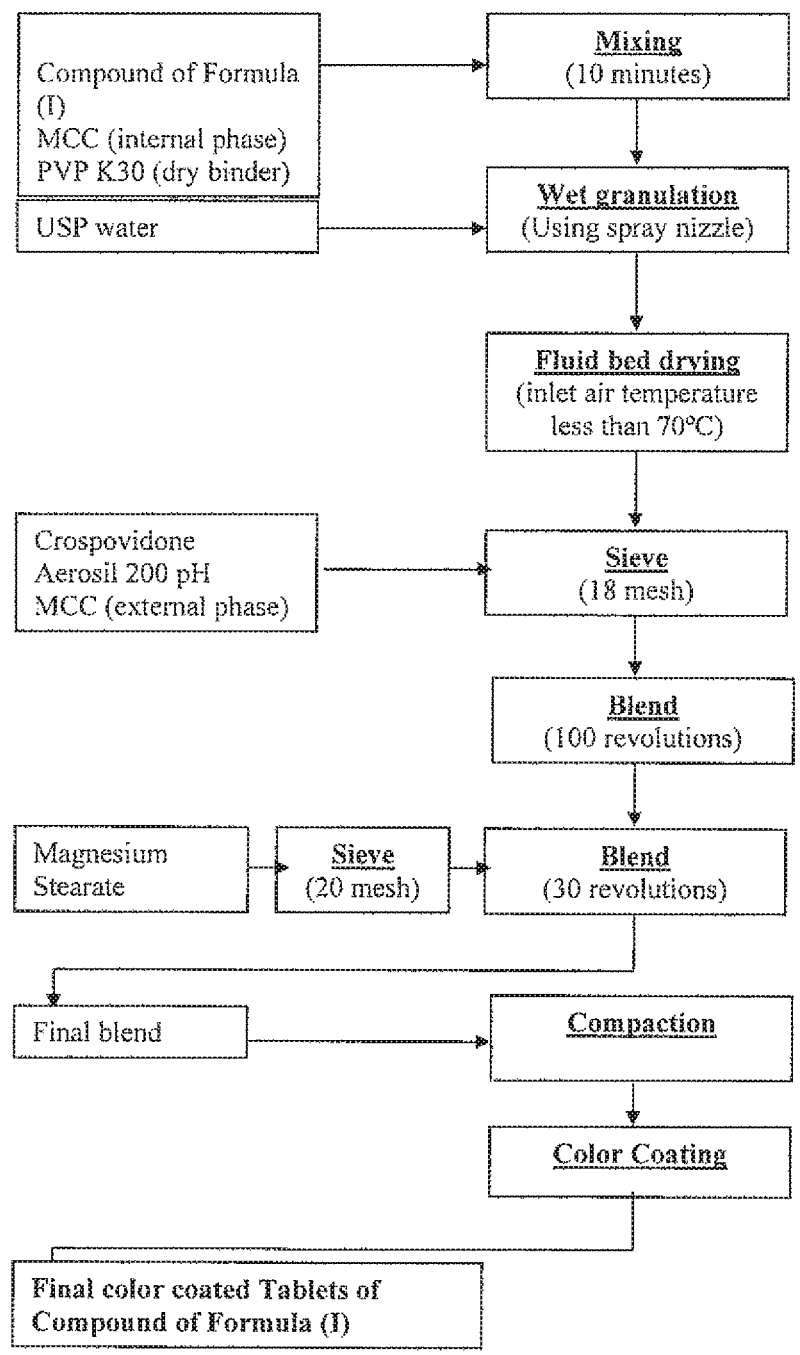
FIG. 19. Illustrates how Compound of Formula (I) and Form H$_A$ of compound of Formula (I) can be made according to general Scheme B.

The below Table 5 illustrates tablet with 300 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide. The tablet might be optionally film coated. The tablet is made by wet granulation as illustrated by Scheme B (FIG. 19).

TABLE 5

| | Component | Percentage* (%) | Amount per tablet (mg) |
|---|---|---|---|
| Internal granular | Compound of Formula (I) | 50.0 | 300.0 |
| | Avicel pH 101 | 27.4 | 164.4 |
| | Polyvinylpyrrolidone (K 30).001 | 5.50 | 33.0 |
| Extra granular** | Avicel pH 102 | 10.0 | 60.0 |
| | Crospovidone.001 | 5.50 | 33.0 |
| | Aerosil 200 PH.001 | 0.60 | 3.60 |
| | Magnesium Stearate PH.001 | 1.00 | 6.00 |
| Opadry 18296 white.001 | | Optional | Optional |
| Total | | 100.0 | 600.0 |

*Note: Percentage of uncoated tablets
**weight adjusted according to internal granular yield
*** total tablet weight = 600 mg

Example 6

The below Table 6 illustrates tablet with 400 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide. The tablet might be optionally film coated. The tablet is made by wet granulation as illustrated by Scheme B (FIG. 19).

TABLE 6

| | Component | Percentage* (%) | Amount per tablet (mg) |
|---|---|---|---|
| Internal granular | Compound of Formula (I) | 61.54 | 400.0 |
| | Avicel pH 101/105 | 17.23 | 112.0 |
| | Polyvinylpyrrolidone (K 30).001 | 5.08 | 33.02 |
| Extra granular** | Avicel pH 102 | 10.00 | 65.0 |
| | Crospovidone.001 | 4.62 | 30.03 |
| | Aerosil 200 PH.001 | 0.53 | 3.45 |
| | Magnesium Stearate PH.001 | 1.00 | 6.50 |
| Opadry 18296 white.001 | | Optional | Optional |
| Total | | 100.0 | 650.0 |

*Note: Percentage of uncoated tablets
**weight adjusted according to internal granular yield
*** total tablet weight = 650 mg

Example 7

The below Table 7 illustrates tablet with 500 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide. The tablet might be optionally film coated. The tablet is made by wet granulation as illustrated by Scheme B (FIG. 19).

TABLE 7

| | Component | Percentage* (%) | Amount per tablet (mg) |
|---|---|---|---|
| Internal granular | Compound of Formula (I) | 66.67 | 500.0 |
| | Avicel pH 101/105 | 14.97 | 112.3 |
| | Polyvinylpyrrolidone (K 30).001 | 4.40 | 33.0 |
| Extra granular** | Avicel pH 102 | 8.46 | 63.45 |
| | Crospovidone.001 | 4.0 | 30.0 |
| | Aerosil 200 PH.001 | 0.50 | 3.75 |
| | Magnesium Stearate PH.001 | 1.00 | 7.50 |
| Opadry 18296 white.001 | | Optional | Optional |
| Total | | 100.0 | 750.0 |

*Note: Percentage of uncoated tablets
**weight will be adjusted according to internal granular yield
*** total tablet weight = 750 mg

Example 8

Figure 20:
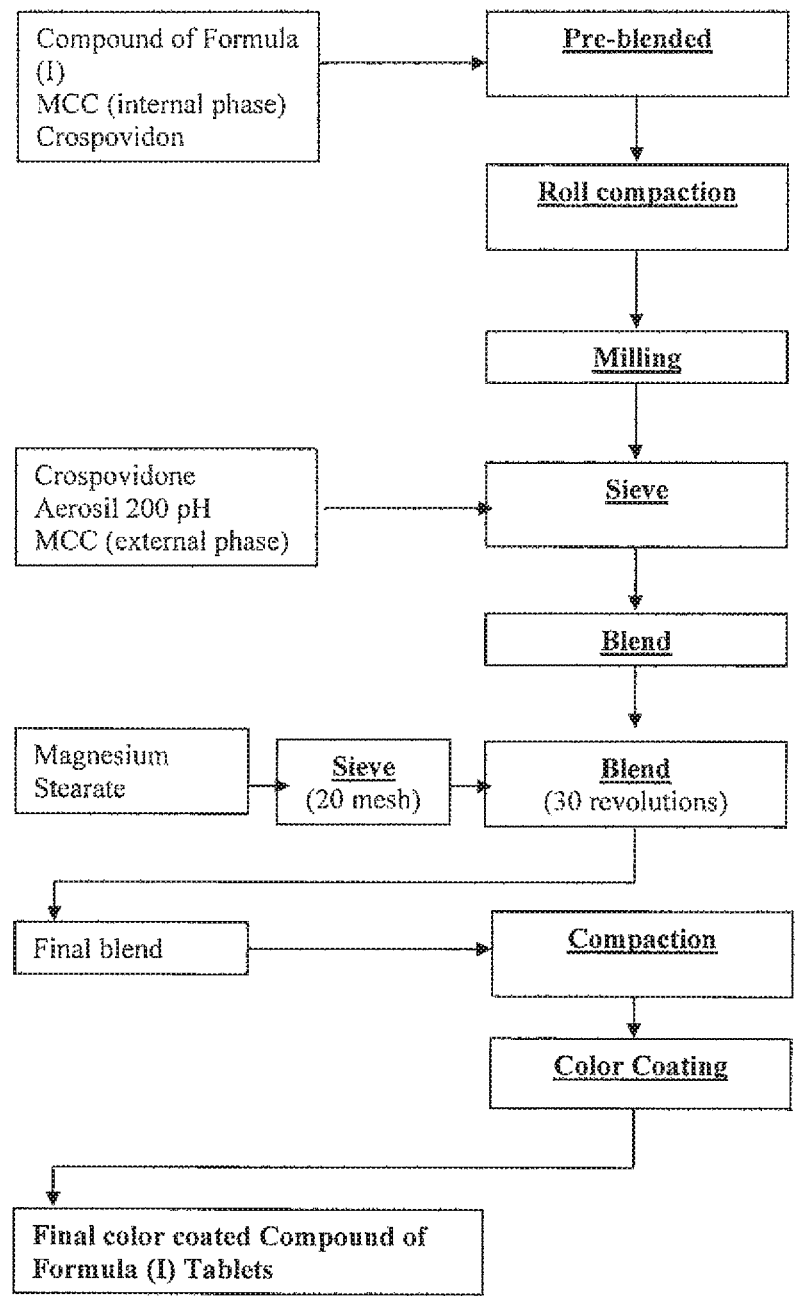
FIG. 20. Illustrates how tablet of manufacturing process with Dry Granulation according to Scheme C.

The below Table 8 illustrates tablet with 300 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide. The tablet might be optionally film coated. The tablet is made by dry granulation as illustrated by Scheme C (FIG. 20).

TABLE 8

| | Component | Percentage* (%) | Amount per tablet (mg) |
|---|---|---|---|
| Internal granular*** | Compound of Formula (I) | 50.0 | 300.0 |
| | Avicel pH 101 | 33.2 | 199.2 |
| | Crospovidone | 2.2 | 13.2 |
| Extra granular** | Avicel pH 102 | 10.0 | 60.0 |
| | Crospovidone.001 | 3.0 | 18.0 |
| | Aerosil 200 PH.001 | 0.60 | 3.60 |
| | Magnesium Stearate PH.001 | 1.00 | 6.00 |
| | Opadry 18296 white.001 | Optional | Optional |
| | Total | 100.0 | 600.0 |

*Note: Percentage of uncoated tablets
**weight adjusted according to internal granular yield
***If a sticking problem is present, a lubricant is added in internal granulation step, such as magnesium stearate, PRUV, etc.

Example 9

The below Table 9 illustrates tablet with 400 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methyl-amino-propionamide. The tablet might be optionally film coated. The tablet is made by dry granulation as illustrated by Scheme C (FIG. 20).

TABLE 9

| | Component | Percentage* (%) | Amount per tablet (mg) |
|---|---|---|---|
| Internal granular*** | Compound of Formula (I) | 61.54 | 400.0 |
| | Avicel pH 101/105 | 21.66 | 140.8 |
| | Crospovidone.001 | 2.2 | 14.3 |
| Extra granular** | Avicel pH 102 | 10.00 | 65.0 |
| | Crospovidone.001 | 3.0 | 19.5 |
| | Aerosil 200 PH.001 | 0.60 | 3.90 |
| | Magnesium Stearate PH.001 | 1.00 | 6.50 |
| | Opadry 18296 white.001 | Optional | Optional |
| | Total | 100.0 | 650.0 |

*Note: Percentage of uncoated tablets
**weight adjusted according to internal granular yield
***If a sticking problem is present, a lubricant is added in internal granulation step, such as magnesium stearate, PRUV, etc.

Example 10

The below Table 10 Illustrates tablet with 500 mg of (S)—N—((S)-1-cyclohexyl-2-{(S)-2-[4-(4-fluoro-benzoyl)-thiazol-2-yl]-pyrrolidin-1-yl}-2-oxo-ethyl)-2-methyl-amino-propionamide. The tablet might be optionally film coated. The tablet is made by dry granulation as illustrated by Scheme C (FIG. 20).

TABLE 10

| | Component | Percentage* (%) | Amount per tablet (mg) |
|---|---|---|---|
| Internal granular | Compound of Formula (I) | 66.67 | 500.0 |
| | Avicel pH 101/105 | 18.07 | 135.5 |
| | Crospovidone | 2.2 | 16.5 |
| Extra granular** | Avicel pH 102 | 8.46 | 63.5 |
| | Crospovidone.001 | 3.0 | 22.5 |
| | Aerosil 200 PH.001 | 0.6 | 4.50 |
| | Magnesium Stearate PH.001 | 1.00 | 7.50 |
| | Opadry 18296 white.001 | Optional | Optional |
| | Total | 100.0 | 750.0 |

*Note: Percentage of uncoated tablets
**weight be adjusted according to internal granular yield
***If a sticking problem is present, a lubricant is added in internal granulation step, such as magnesium stearate, PRUV, etc.

Example 11

Compound of Formula (I) and Form $H_A$ of compound of Formula (I) are made according to general Scheme A, and as detailed below. The notation of the different compounds can be found in Scheme A.

B2 to B4

Charge a 1-L Argonaut reactor with 27 g of 2-(S)-1-tert-butoxycarbonyl-pyrrolidin-2-yl)-thiazole-4-carboxylic acid (B1), 9.7 g of N,O-dimethylhydroxylamine hydrochloride, and 157 g of N,N-dimethylformamide. Warm the suspension at 24±3° C. for 20 min to give a homogenous solution. Cool the contents to 20±3° C. over 15 min, then add 35 g of triethylamine into pot at 20±3° C. over 15 min to give a light tan suspension. Add 69 g of 1-propylphosphoric acid cyclic anhydride/ethyl acetate solution (50 wt. %) into pot at 20±3° C. over 30 min. Stir the slurry at 20±3° C. for 30 min. After Process Steering Control #1 has passed, add 200 g of water slowly into pot at 20±3° C. over 20 min to give a homogenous solution. Add 360 g of toluene into pot and stir the mixture at 20±3° C. for 15 min. Discard the bottom aqueous layer and rag layer. Wash the top organic layer with a solution of 1 g of sodium bicarbonate in 100 g of water. Discard the bottom aqueous layer. Wash the top organic layer twice with a total amount of 200 g of water. Concentrate the toluene extract at 60±3° C. (10 mbar) to a viscous oil (~36 g). Flush the residue twice with a total amount of 66 g of toluene at 60±3° C. (10 mbar) to give 33.5 g of (S)-2-[4-(methoxy-methyl-carbamoyl)-thiazol-2-yl]-pyrrolidine-1-carboxylic acid tert-butyl ester (B2) as a yellow-tan viscous oil. Add 90 g of toluene into pot. Distill toluene (~11.5 g) off from the contents at 60±5° C. (10 mbar) to give 112 g of B2/toluene solution (~25 wt %). After PSC #2 and water content (KF, $H_2O$<0.1%) have passed, drum up B2/toluene solution (~25 wt %) for the further B4 preparation.

B2 to B4

Preparation of Acetic Acid Solution:

Charge to a 500 mL round-bottom inerted with nitrogen with 156.9 g of water and 39.2 g of glacial acetic acid. Stir the solution for 5 min and store until needed.

Reaction of B2 with B3:

To 0.5 L, 4-Necked flask equipped with nitrogen purge, cooling bath, overhead stirring and internal temperature probe charge a preformed solution of 109.8 g of B2 in 329.3 g of toluene. Cool the solution to −10° C.±5° C. Add a solution of 386 g of B3 (1.0 M solution in THF) over a period of 2.0 h maintaining −10±5° C. Stir the contents of the flask for 1.0 h at −10° C.±5° C. 1 Charge 19.6 g of 20 wt % acetic acid solution in water over a period of 0.5 h. Next charge 176 g of 20 wt % acetic acid solution in water over a period of 1.5 h maintaining −10±5° C. Charge 200 g of water over a period of 0.5 h maintaining the temperature between −10±5° C. Stir the phases for 1 h. Warm the batch to 25±3° C. over 0.5 h. Stop agitation and allow the phases to separate. Remove the bottom aqueous layer. Charge 200 g of water. Stir the phases for 5 min. Stop agitation and allow the phases to separate. Remove the bottom aqueous layer. Charge 200 g of water. Stir the phases for 5 min. Stop agitation and allow the phases to separate. Remove the bottom aqueous layer. Concentrate the organic layer to 500 mL total volume. Add 435 g isopropyl acetate. Concentrate the organic layer to 500 mL total volume. Add 435 g isopropyl acetate. Concentrate the organic layer to 500 mL total volume. Use the resulting solution directly for the following step.

B4 to B5

To a 0.5 L round bottom flask inerted with nitrogen and equipped with a stirring bar and ice bath charge 192.0 g of isopropanol. Cool the batch to 10° C.±3° C. and charge by vacuum 48.4 g of HCl gas (weighed by difference in cylinder weight). Stir the solution for 15 min at 10° C.±3° C. and warm the batch to 20° C.±3° C. Vent the solution with nitrogen if a vacuum is present or to the scrubber if pressure is greater than atmospheric.

Formation of B5

To a separate 0.5 L, 4-necked flask equipped with nitrogen purge, cooling bath, overhead stirring and internal temperature probe, charge a preformed solution of 55.0 g of B4 in 231.0 g of toluene and isopropyl acetate, and raise the internal temperature to 27° C.±3° C. Add a preformed solution of 168 g of 5.5M of HCl in isopropanol over a period of 10 min maintaining 27° C.±3° C. Stir the contents of the flask for 5.5 h at 27° C.±3° C. Cool the reaction mixture to 20° C.±5° C. and concentrate the mixture to 250 mL total volume at 100-120 mbar (Jacket temperature 35-45° C.). Add 217.0 g isopropyl acetate. Concentrate the organic layer to 250 mL total volume (100-120 mbar Jacket temperature 35-45° C.). Add 217.0 g of isopropyl acetate. Filter the resulting solids and wash with 130.0 g of isopropyl acetate. Place the solids in an oven at 80° C.±3° C. for 8 h to give 40.1 g of B5.

B5 to B6

Charge a 2 L Argonaut reactor with 67.98 g (200 mmol) of 85 containing toluene and iPrOAc (total 8.67% by weight), 75.70 g of Z5a (210 mmol) containing 5.01% water, 60.9 g of DMT-MM (220 mmol), and 700 mL (631.4 g) of ethyl acetate. Stir and cool the suspension to −1±3° C., slowly add 50.6 g (0.5 mol) of N-methylmorpholine while maintaining temperature at −1±3° C. over 40 min. Stir and hold at −1±3° C. for 30 min., then warm to 19±3° C. and hod at this temperature for 3.5 h. Take a sample for Process Steering Control. If PSC passes, slowly add 300 g of water, and 300 mL (270.6 g) of ethyl acetate while maintaining the temperature at 20±3° C. Stir at 20±3° C. for 30 min, then separate the two layers. Keep the top layer since B6 is in this organic phase. Wash the organic layer with 250 mL (260 g) of 1 N NaOH solution. Separate the bottom layer (aqueous). Add 250 mL (254.6 g) of 2 N HCl solution to the top layer and stir for 15 min. Separate the bottom layer. Add 250 mL (286.6 g) of brine. To the top layer and stir for 15 min. Separate the bottom layer and evaporate the organic layer to 200 mL left in the flask under vacuum at 30° C. at 735 mm. Add 300 mL (270.6 g) of ethyl acetate and evaporate the organic layer under vacuum at 30° C. at 735 mm until 400~500 mL of residue left in the flask which is used directly in next step.

B6 to B7 (Compound of Formula (I))

Charge a 2 L Argonaut reactor with 120 g (20 mmol) of crude B6 in 360.8 g (400 mL) of ethyl acetate. Heat the solution to 45±3° C., slowly add 109.1 g (120 mL) of HCl (5-6 N) in isopropyl alcohol while maintaining temperature at 45±3° C. over 30 min. Stir and hold at 45±3° C. for 2 h. Take a sample for Process Steering Control. If PSC passes, cool the reaction mixture to 18±3° C. Slowly add this solution to a 2 L Argonaut reactor containing 82.9 g of potassium carbonate in 500 g of water while maintaining the temperature at 5±3° C. Stir at 5±3° C. for 30 min, add 451 g (500 mL) of ethyl acetate. Warm the solution to 20±3° C. and hold at this temperature for 1 h. Separate the two layers. Keep the top layer since B7 is in this organic phase. Wash the organic layer with 286.6 g (250 mL) of brine. Separate the bottom layer (aqueous). Concentrate the top organic layer to 500 mL under vacuum at 30° C. Slowly add 1368 g (2 L) of heptanes while maintaining the temperature at 30±3° C. Cool the suspension to 18±3° C. and hold at 18±3° C. for 1 h. Filter the solids and wash the solids with 136 g (200 mL) of heptanes containing octastat. Dry the solids in an oven at 45° C. for 16 h to give 80 g of B7 in 80% yield.

B7 to Form $H_4$ of Compound of Formula (I)

Charge a 2 L Argonaut reactor with 78.0 g of B7 and 616.2 g (780 mL) of ethanol (200 proof). Heat the solution to 30±3° C., add 100 g of water. Filter the solution, then slowly add 1750 g of water while maintaining temperature at 30±3° C. over 40 min. Cool the suspension to 18±3° C. and hold at this temperature for 2 h. Filter the solids and wash the solids with 60 mL of 20% ethanol in water. Dry the solids in an oven at 45° C. and 25 mbar for 16 h to give 72 g of Form $H_4$ of compound of Formula (I) in 90% yield.

Example 12

Equilibration at Ambient Temperature

A screen is conducted with many different solvents. About 50-60 mg of Form $H_4$ of compound of Formula (I) formed in Example 11 is equilibrated with 1 ml of each solvent for at least 24 h at ambient temperature. More Form $H_4$ of compound of Formula (I) is added if the solid dissolved, until a slurry is obtained. The equilibrated slurries are filtered and the solids are dried for 10 min in the open air. Form A is formed using certain solvents as detailed below.

| Solvent | XRDP | Comments |
| --- | --- | --- |
| Acetone | + | Form A |
| Acetonitrile | + | Form A |
| Ethanol abs. | + | Form A |
| Ethyl acetate | + | Form A |
| Methanol | + | Form A |
| Methyl isobutyl ketone | + | Form A |

Explanation
"+" change detected

Example 13

Equilibration at 50° C.

A screen is conducted with many different solvents. About 50-60 mg of Form $H_4$ of compound of Formula (I) formed in Example 11 is equilibrated with 1 ml of each solvent for at least 24 h at 50° C. More Form $H_4$ of compound of Formula (I) is added if the solid dissolved, until a slurry is obtained. The equilibrated slurries are filtered and the solids are dried for 10 min in the open air. Forms A and B are formed using certain solvents as detailed below.

| Solvent | XRDP | DSC and/or TGA | Comments |
|---|---|---|---|
| Acetone | + | | Form A |
| Acetonitrile | + | | Form A |
| Ethanol abs. | + | | Form A |
| Ethyl acetate | + | | Form A |
| Heptane | + | | Form B |
| Propan-2-ol | + | | Form A |
| Methanol | + | | Form A |
| Methyl isobutyl ketone | + | | Form A |
| Isopropyl acetate | + | | Form A |
| Methyl tert-butyl ether | + | On another sample 1373-118-6__eq_MtBE: 147.45° C. 150.8 (exo, peak max) 154.2° C./ 0.24% | Form A |

Explanation
"+" change detected

Example 14

Evaporative Crystallization at Ambient Temperature

The equilibrated slurries in Example 12 are filtered and the filtered clear solutions are left at ambient temperature to evaporate the solvents. Form A is formed with ethyl acetate.

Example 15

Crystallization from Hot Saturated Solutions

Concentrated (>50 mg/ml) or saturated solutions at 60° C. are filtered and then cooled to 4° C. The precipitates are filtered, air dried and investigated. Forms B, C, or D are formed with certain solvents as detailed below.

| Solvent | XRDP | DSC and/or TGA | Comments |
|---|---|---|---|
| Acetone | + | After air drying: 127.7° C. (broad) 154.4° C./ 0.04% | Solvate, converts to D upon vacuum drying at 65° C. |
| Acetonitrile | + | 149.5° C. 151.6° C. (exo, peak max) 154.2° C./ 0.05% | Form C |
| Ethyl acetate | + | 141.9° C. 147.5° C. (exo, peak max) 153.0° C./ 0.8% | Solvate, converts to D upon vacuum drying at 65° C. |
| Methyl isobutyl ketone | + | 153.8° C./ 0.2% | Form B |

Explanation
"+": change detected

Example 16

Precipitation by Addition of Antisolvent

Different solvent combinations are tested. The Form $H_A$ of compound of Formula (I) is dissolved in a medium where the solubility is high, and a solvent in which compound of Formula (I) is highly insoluble is added. Each of the precipitate is filtered and the solids are dried for 10 min in the open air. Forms A or D are formed with certain solvents combinations as detailed below.

| Solvent | Non-solvent (volume ratio to solvent) | XRPD | DSC and/or TGA | Comments |
|---|---|---|---|---|
| Acetone | Heptane (7) | + | 143.0° C. 148.8° C. (exo, peak max) 153.7° C./ 0.3% | Form A |
| Ethyl acetate | Heptane (3) | + | 139.6° C. 146.6° C. (exo, peak max) 154.7° C./ 0.07% | Form A |
| Tetrahydrofuran | Heptane (3) | + | 144.2° C. 146.9° C. (exo, peak max) 154.2° C./0.5% | Solvate, converts to Form D upon vacuum drying at 65° C. |

Explanation
"+": change detected

Example 17

The crystalline forms HA, A, B, C, and D obtained in Examples 11-16 are analyzed by various standard methods: XPRD, DSC, TGA, Microscopy. Water sorption and desorption is also examined. The results are shown in FIGS. 1-16.

We claim:
1. Crystalline Form A of (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide, described by Formula (I):

Compound of Formula (I)

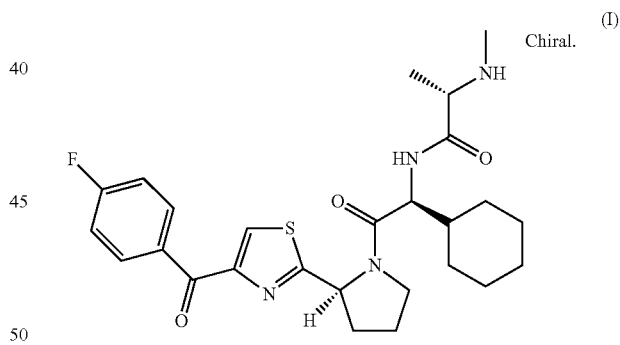

2. The crystalline Form A of claim 1 having a powder x-ray diffraction pattern comprising three or more 2θ values selected from the group consisting of 5.3±0.2, 6.7±0.2, 9.1±0.2, 13.4±0.2, 13.6±0.2, 15.0±0.2, 15.3±0.2, 17.4±0.2, 18.2±0.2, 18.7±0.2, 18.9±0.2, 20.2±0.2, 21.3±0.2, 21.8±0.2, 23.0±0.2, 23.5±0.2, 24.6±0.2, and 27.6±0.2, at ambient temperature.

3. The crystalline Form A of claim 1 having a powder x-ray diffraction pattern at ambient temperature, substantially in accordance with that shown in FIG. 1.

4. The crystalline Form A of claim 1 having a differential scanning calorimetry (DSC) thermogram substantially in accordance with that shown in FIG. 3.

5. The crystalline Form A of claim 1 having a thermo gravimetric analysis (TGA) diagram substantially in accordance with that shown in FIG. 3.

6. A pharmaceutical formulation comprising active ingredient (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide of crystalline Form A or a pharmaceutically acceptable salt thereof in an amount higher than 100 mg, and pharmaceutically acceptable excipients thereof.

7. The formulation of claim 6, wherein (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is in an amount higher than 125 mg.

8. The formulation of claim 6, wherein (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is in an amount higher than 200 mg.

9. The formulation of claim 6, wherein (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is in an amount higher than 250 mg.

10. The formulation of claim 6, wherein (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is in an amount higher than 300 mg.

11. The formulation of claim 6, wherein (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is in an amount higher than 400 mg.

12. The formulation of claim 6, wherein (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide is in an amount higher than 500 mg.

13. The formulation of claim 6, made by wet granulation.

14. The formulation of claim 6, made by dry granulation.

15. The formulation of claim 6 further comprising a surfactant.

16. The formulation of claim 6 further comprising an acid.

17. The formulation of claim 6 further comprising an antioxidant.

18. The formulation of claim 6, wherein the pharmaceutical formulation is a solid oral dosage form, and wherein the (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide or its salt is in small particle form with a median particle size of 10 nm to 40 microns.

19. The pharmaceutical formulation of claim 6, further comprising a disintegrant or super disintegrant.

20. The pharmaceutical formulation of claim 6, further comprising a glidant, a lubricant, or both a glidant and a lubricant.

21. The pharmaceutical formulation of claim 6, wherein the active ingredient is more than 40% (w/w) of the total formulation.

22. The pharmaceutical formulation of claim 6, wherein the active ingredient is more than 50% (w/w) of the total formulation.

23. The pharmaceutical formulation of claim 6, wherein the active ingredient is more than 60% (w/w) of the total formulation.

24. The pharmaceutical formulation of claim 6, wherein the active ingredient is more than 70% (w/w) of the total formulation.

25. The pharmaceutical formulation of claim 6, wherein the active ingredient is more than 80% (w/w) of the total formulation.

26. A pharmaceutical formulation comprising an internal granular portion and an extra granular portion,
wherein the internal granular portion comprises:
(1) 40-60% (w/w) active ingredient (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide of crystalline Form A or a pharmaceutically acceptable salt thereof in an amount higher than 100 mg, and pharmaceutically acceptable excipients thereof,
(2) 15.0-37.4% (w/w) filler, and
(3) 3.0-10.0% (w/w) binder; and
wherein the extra granular portion comprises:
(1) up to 22.4% (w/w) of binder or filler,
(2) 2.0-80% (w/w) of disintegrant, and
(3) 0.5-1.5% (w/w) of lubricant.

27. A pharmaceutical formulation comprising active ingredient (S)—N—((S)-1-cyclohexyl-2-{(S)-2-[4-(4-fluoro-benzoyl)-thiazol-2-yl]-pyrrolidin-1-yl}-2-oxo-ethyl)-2-methylamino-propionamide of crystalline Form A or a pharmaceutically acceptable salt thereof and pharmaceutically acceptable excipients thereof.

* * * * *